United States Patent
Jemmerson

(10) Patent No.: US 7,416,850 B2
(45) Date of Patent: Aug. 26, 2008

(54) CYTOCHROME C AND LEUCINE-RICH ALPHA-2-GLYCOPROTEIN-1 ASSAYS, METHODS AND ANTIBODIES

(76) Inventor: Ronald R. Jemmerson, 3211 E. 45th St., Minneapolis, MN (US) 55406

( * ) Notice: Subject to any disclaimer, the term of this patent is extended or adjusted under 35 U.S.C. 154(b) by 0 days.

(21) Appl. No.: 11/627,164

(22) Filed: Jan. 25, 2007

(65) Prior Publication Data
US 2007/0184503 A1    Aug. 9, 2007

Related U.S. Application Data

(60) Provisional application No. 60/761,808, filed on Jan. 25, 2006.

(51) Int. Cl.
G01N 33/53    (2006.01)
(52) U.S. Cl. ............... 435/7.1; 435/7.92; 435/7.94; 436/501; 436/518; 436/164
(58) Field of Classification Search ............... 435/7.1, 435/7.92–7.95, 969; 436/501, 518, 523–528, 436/164
See application file for complete search history.

(56) References Cited

OTHER PUBLICATIONS

Adachi, N., et al., "Serum cytochrome c level as a prognostic indicator in patients with systemic inflammatory response syndrome", *Clinica Chimica Acta*, (2004),342:127-136.
Barczyk, K., et al., "Serum cytochrome c indicates in vivo apoptosis and can serve as a prognostic marker during cancer therapy", *International Journal of Cancer*, (2005),116:167-173.
Ben-Ari, Z., et al., "Circulating soluble cytochrome c in liver disease as a marker of apoptosis", *Journal of Internal Medicine*, (2003),254:168-175.
Boehning, D., et al., "Cytochrome c binds to inositol (1,4,5) trisphosphate receptors, amplifying calcium-dependent apoptosis", *Nature Cell Biology*, (2003),5:1051-1061.
Bruey, J., et al., "Hsp27 negatively regulates cell death by interacting with cytochrome c", *Nature Cell Biology*, (2000),2:645-652.
Cummings, C., et al., "Serum leucine-rich alpha-2-glycoprotein-1 binds cytochrome c and inhibits antibody detection of this apoptotic marker in enzyme-linked immunosorbent assay", *Apoptosis*, (2006),11:1121-1129.
Haupt, H., et al., "Isolierung und Charakterisierung eines bisher unbekannten leucinreichen 3.1S-a2-Glykoproteins aus Humanserum", *Hoppe-Seyler's Z Physiol Chem*, (1977),358:639-646.
Jemmerson, R., et al., "Cytochrome c release from CNS mitochondria and potential for clinical intervention in apoptosis-mediated CNS diseases", *Antiox. Redox Signal*, (2005),7:1158-1172.
Jemmerson, R., et al., "Release of intact, monomeric cytochrome c from apoptotic and necrotic cells", *Cell Death Differentiation*, (2002),9:538-548.
Kluck, R., et al., "Determinants of cytochrome c pro-apoptotic activity—The role of lysine 72 trimethylation", *Journal of Biological Chemistry*, (2000),275:16127-16133.

Kobe, B, et al., "The leucine-rich repeat as a protein recognition motif", *Current Opinion Structural Biology*, (2001),11:725-732.
Li, P., et al., "Cytochrome c and dATP-dependent formation of Apaf-1/Caspase-9 complex initiates an apoptotic protease cascade", *Cell*, (1997),91:479-489.
Liu, X., et al., "Induction of apoptotic program in cell-free extracts: Requirement for dATP and cytochrome c", *Cell*, (1996),86:147-157.
Newmeyer, D. D., et al., "Mitochondria: Releasing power for life and unleashing the machineries of death", *Cell*, (2003),112:481-490.
Nunoi, H., et al., "Apoptosis under hypercytokinemia is a possible pathogenesis in influenza-associated encephalopathy", *Ped. Internat.*, (2005),47:175-179.
Nur-E-Kamal, A., et al., "Nuclear translocation of cytochrome c during apoptosis", *Journal of Biological Chemistry*, (2004),279:24911-24914.
O'Donnel, L. C., et al., "Molecular characterization and expression analysis of leucine-rich a2-glycoprotein, a novel marker of granulocytic differentiation", *Journal of Leukocyte Biology*, (2002),72:478-485.
Pullerits, R., et al., "Extracellular cytochrome c, a mitochondrial apoptosis-related protein, induces arthritis", *Rheumatol*, (2005),44:32-39.
Renz, A., et al., "Rapid extracellular release of cytochrome c is specific for apoptosis and marks cell death in vivo", *Blood*, (2001),98:1542-1548.
Takahashi, N., et al., "Periodicity of leucine and tandem repetition of a 24-amino acid segment in the primary structure of leucine-rich a2-glycoprotein of human serum", *Proceedings of the National Academy of Science of the United States of America*, (1985),82:1906-1910.
Zou, H., et al., "Apaf-1, a human protein homologous to C. elegans CED-4 participates in cytochrome c-dependent activation of caspase-3", *Cell*, (1997),90:405-413.

*Primary Examiner*—Gailene Gabel
*Assistant Examiner*—Gary W Counts
(74) *Attorney, Agent, or Firm*—Pauly, DeVries Smith & Deffner, L.L.C.

(57) ABSTRACT

The present invention relates generally to assays and methods involving Cytochrome c (Cyt c) and leucine-rich alpha-2-glycoprotein-1 (LRG), and related antibodies. In an embodiment, the invention includes a method of detecting LRG in a sample, the method including disposing Cyt c on a substrate; contacting the sample with the Cyt c; contacting bound components of the sample with an antibody or antibody fragment specific for LRG; and quantitating the amount of the antibody or antibody fragment bound to LRG. In an embodiment, the invention includes a method of purifying or enhancing the purity of LRG from a sample, the method including contacting the sample with Cyt c; forming a complex between LRG in the sample and Cyt c; removing uncomplexed components of the sample; releasing LRG from the complex with Cyt c; and collecting the released LRG. In an embodiment, the invention includes an isolated antibody produced by a hybridoma cell line (ATCC Accession Number PTA-8131), or antibody fragment thereof that specifically binds to LRG. In an embodiment, the invention includes a kit comprising an antibody that specifically binds to LRG, or a fragment thereof that specifically binds to LRG, and a compartment, wherein the antibody or fragment is contained within the compartment. Other embodiments are described herein.

15 Claims, 10 Drawing Sheets

CYTOCHROME C AND LEUCINE-RICH ALPHA-2-GLYCOPROTEIN-1 ASSAYS, METHODS AND ANTIBODIES

This application claims the benefit of U.S. Provisional Application No. 60/761,808, filed Jan. 25, 2006, the contents of which are herein incorporated by reference.

GOVERNMENT FUNDING

The present invention was made partially with government support under Grant No. 5R21-NS45589, awarded by the National Institute of Neurological Disorders and Stroke, National Institutes of Health. The Government may has certain rights in this invention.

FIELD OF THE INVENTION

The present invention relates generally to Cytochrome c (Cyt c) and leucine-rich alpha-2-glycoprotein-1 (LRG). More specifically, the present invention relates to assays and methods involving Cyt c and LRG, and related antibodies.

BACKGROUND OF THE INVENTION

Cancer is a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. Cancer may affect people at all ages, but risk tends to increase with age, due to the fact that DNA damage becomes more apparent in aging DNA. According to the American Cancer Society, well over one million new cases of cancer are diagnosed each year in the United States. Cancer causes over a half million deaths each year in the United States, making it the second leading cause of death.

Many different molecules are thought to play a role in the complex pathogenesis of cancer. The mitochondrial protein cytochrome c (Cyt c) is one such molecule and is believed to be important in the suppression of cancer development because of its role as an important initiator/amplifier of programmed cell death or apoptosis. Specifically, following its translocation to the cytoplasm, Cyt c binds Apaf-1 and serves as a cofactor in caspase-9 activation (Liu et al., Cell, 1996; 86: 147-157). Cyt c has considerable clinical potential as a serum marker for aberrant apoptosis. In several clinical trials, an increase in serum Cyt c has been observed in a variety of patients including those with cancer, myocardial infarcts, apoptosis-associated liver disease, systemic inflammatory response syndrome, and influenza virus-induced encephalopathy (reviewed by Jemmerson et al., Antiox. Redox Signal., 2005; 7: 1158-1172).

For at least these reasons, a need exists for sensitive methods of detecting Cyt c in samples and antibodies for implementing the same. A need also exists for methods of detecting molecules that interact with Cyt c.

SUMMARY OF THE INVENTION

The present invention relates to assays and methods involving Cytochrome c ("Cyt c") and its ligand, leucine-rich alpha-2-glycoprotein-1 ("LRG"), and related antibodies. In an embodiment, the invention includes a method of detecting LRG in a sample, the method including disposing Cyt c on a substrate; contacting the sample with the Cyt c; contacting bound components of the sample with an antibody or antibody fragment specific for LRG; and detecting the antibody or antibody fragment bound to LRG.

In an embodiment, the invention includes a method of purifying or enhancing the purity of LRG from a sample, the method including contacting the sample with Cyt c; forming a complex between LRG in the sample and Cyt c; removing uncomplexed components of the sample; releasing LRG from the complex with Cyt c; and collecting the released LRG.

In an embodiment, the invention includes an isolated antibody produced by a hybridoma cell line having ATCC Accession Number PTA-8131, or antibody fragment thereof that specifically binds to LRG and to LRG when ligated to Cyt c.

In an embodiment, the invention includes a kit comprising an antibody that specifically binds to LRG, or a fragment thereof that specifically binds to LRG, and a compartment, wherein the antibody or fragment is contained within the compartment.

BRIEF DESCRIPTION OF THE DRAWINGS

In FIG. 5A, lane 1, 96-99% pure BSA adsorbed on lysozyme; lane 2, 96-99% pure BSA adsorbed on Cyt c; lane 3, >99% BSA adsorbed on lysozyme; lane 4, 99% BSA adsorbed on Cyt c; m.w., molecular weight markers. BSA was identified by MALDI-TOF MS.

DETAILED DESCRIPTION OF ILLUSTRATIVE EMBODIMENTS OF THE INVENTION

Figure 1A:
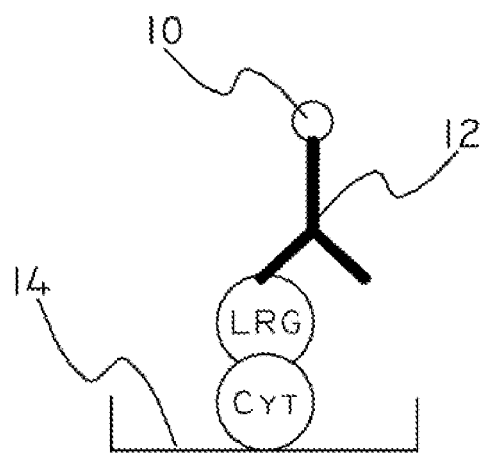
FIGS. 1A-1H are schematic views of assay components in accordance with various embodiments of the invention.

Many different molecules are thought to play a role in the complex pathogenesis of cancer. The mitochondrial protein cytochrome c (Cyt c) is one such molecule. In addition to its role in electron transport, Cyt c is an important initiator/amplifier of programmed cell death or apoptosis (Newmeyer and Ferguson-Miller, Cell 2003; 112: 481-490). As a moonlighting protein, Cyt c has been implicated in a number of apoptotic functions (reviewed in Jemmerson et al., Antiox. Redox Signal. 2005; 7: 1158-1172). Following its translocation to the cytoplasm Cyt c binds Apaf-1 and serves as a cofactor in caspase-9 activation (Liu et al., Cell 1996; 86: 147-157; Zou et al., Cell 1997; 90: 405-413; and Li et al., Cell 1997; 91: 479-489). Cyt c has also been reported to enhance calcium release by inositol trisphosphate receptors in the endoplasmic reticulum (Boehning et al, Nat. Cell Biol. 2003; 5: 1051-1061) and to induce acetylated histone 2A efflux from the nucleus into the cytoplasm (Nur-E-Kamal et al., J. Biol. Chem. 2004; 279: 24911-24914). Phospholipid-bound Cyt c has increased peroxidase activity and has been suggested to be involved in oxidation of cardiolipin allowing for Cyt c translocation from mitochondria and in oxidation of phosphatidylserine leading to externalization of the phospholipid on the plasma membrane (Kagan etal., Free Rad. Biol. Med. 2004; 37: 1963-1985).

Cyt c is ultimately released from apoptotic cells in vitro as a monomer in its native conformation (Jemmerson et al., Cell Death Differ. 2002; 9: 538-548). This release begins to occur soon after changes in the plasma membrane that signal uptake by phagocytic cells predicting that Cyt c would appear outside apoptotic cells in vivo, particularly in situations where apoptosis is increased or when phagocytosis is defective (Renz et al., Blood 2001; 98: 1542-1548). Extracellular Cyt c may play a role in inflammation as it has been reported to cause arthritis when injected into mice and to induce in vitro the expression of a key pro-inflammatory transcription factor, NF-κB, although at a relatively high concentration of Cyt c (100 μg/ml) (Pullerits et al., Rheumatology 2005; 44: 32-39).

Cyt c has considerable clinical potential as a serum marker for aberrant apoptosis (reviewed in Jemmerson et al., Antiox. Redox Signal. 2005; 7: 1158-1172). In several clinical trials an increase in serum Cyt c has been observed in a variety of patients including those with cancer (Renz et al., Blood 2001; 98: 1542-1548; and Barczyk et al., Int. J. Cancer 2005; 116: 167-173), myocardial infarcts (Gvatua et al., Ter. Arkh. 1990; 62: 58-61; and Alleyne et al., Appl. Biochem. Biotech. 2001; 90: 97-105), apoptosis-associated liver disease (Ben-Ari et al., J. Intern. Med. 2003; 254: 168-175), systemic inflammatory response syndrome (Adachi et al., Clin. Chim. Acta 2004; 342: 127-136), and influenza virus-induced encephalopathy (Nunoi et al., Pediatr. Int. 2005; 47: 175-179).

Sandwich ELISA (enzyme-linked immunosorbent assay) is one technique often used to quantify antigens in a complex solution such as serum (Engvall, Meth. Enzymol. 1980; 70: 419-439). Several sandwich ELISA kits for Cyt c are commercially available and these assays have been employed to detect Cyt c in clinical samples (Barczyk et al., Int. J. Cancer 2005; 116: 167-173; Gvatua et al., Ter. Arkh. 1990; 62: 58-61; Alleyne et al., Appl. Biochem. Biotech. 2001; 90: 97-105; Ben-Ari et al., J. Intern. Med. 2003; 254: 168-175; Adachi et al., Clin. Chim. Acta 2004; 342: 127-136; and Nunoi et al., Pediatr. Int. 2005; 47: 175-179. However, it has been found that serum interferes with the quantification of Cyt c in currently available sandwich ELISA reducing the sensitivity of Cyt c detection (see below; Cummings et al., Apoptosis, 2006; 11: 1121-1129, published on-line May 9, 2006). This may undermine the usefulness of Cyt c as a prognostic indicator when employing currently available assays, particularly in less acute forms of apoptotic diseases where the level of circulating Cyt c may be only slightly elevated.

Figure 1B:
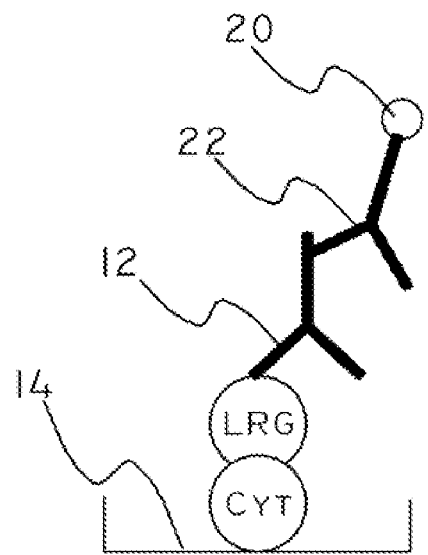
Figure 2:
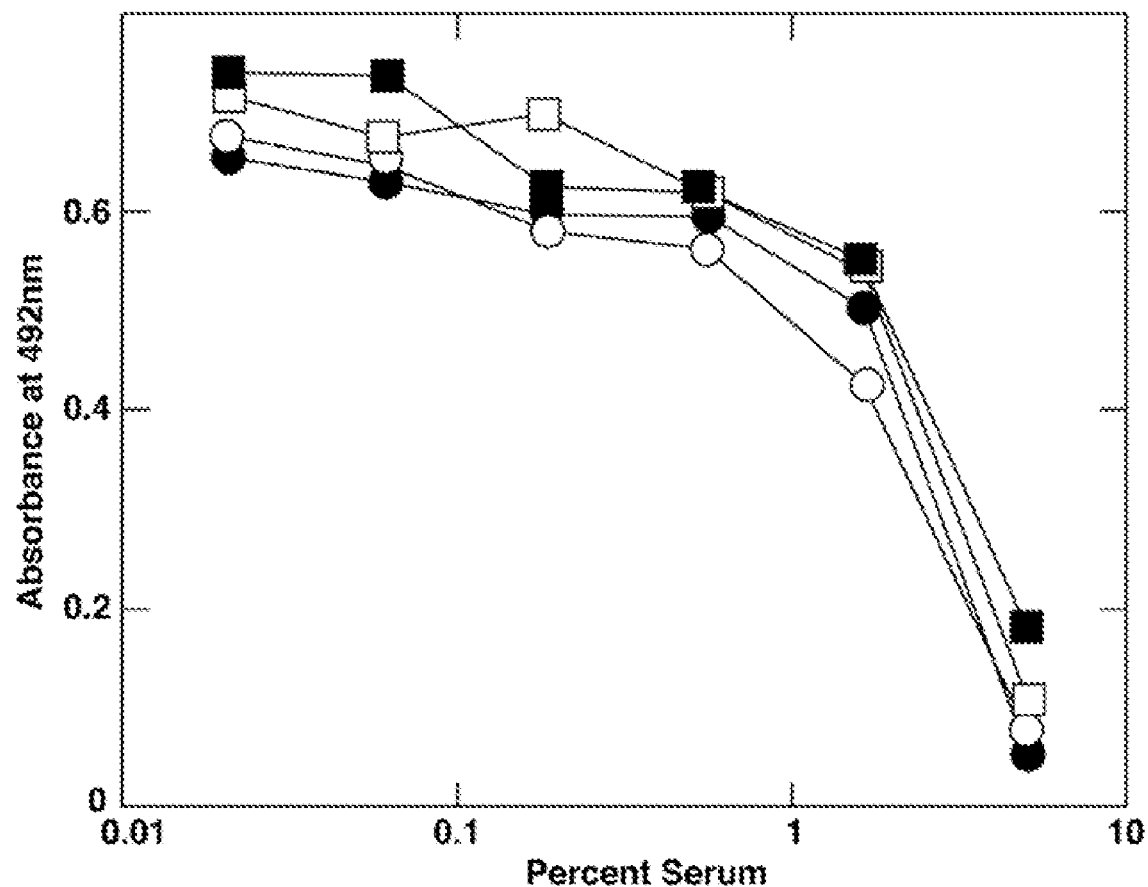
FIG. 2 demonstrates that the inhibitory factor for rat Cyt c detection in sandwich ELISA, later identified as LRG, is present in human (●), mouse (○), and both normal (■) and gamma globulin-free (□) horse sera. Inhibition was also observed with fetal bovine serum (not shown). The values plotted represent the averages of triplicate readings with an average S.D.=0.028.

The present disclosure includes the demonstration that LRG (leucine-rich alpha-2-glycoprotein-1) is a ligand for Cyt c. LRG acts as an inhibitory factor, reducing the sensitivity of various assays for the detection of Cyt c in serum samples as shown in FIG. 2. It is disclosed herein that LRG also competes with Apaf-1 for binding Cyt c in vitro, as demonstrated in FIG. 9, and this function may be physiologically relevant. LRG could be a survival factor used by some cancer cells to block the pro-death activity of Cyt c and used by inflammatory cells such as neutrophils to extend their half-life during infection. Beyond its role as an inhibitory factor, LRG has physiological properties that make it a desirable target for detection by itself. For example, LRG transcripts are detected in human neutrophils (see O'Donnell et al., Journal of Leukocyte Biology. 2002; 72:478-485), the liver (see for example, NCBI GEO Profiles databases GDS565 and GDS1443), and certain cancer cells (see for example, NCBI GEO Profiles databases GDS389 and GDS1523). It is disclosed herein that LRG is increased in the sera of a variety of cancer patients, as demonstrated in example 4, using an embodiment similar to that illustrated in FIG. 1B.

Aspects of the present invention can include assays dependent on the binding of Cyt c to LRG. Aspects of the invention can specifically include assays for detecting Cyt c, LRG, and/or complexes of Cyt c and LRG in a sample. Many different assays are contemplated. In an embodiment, the invention includes a method of detecting LRG in a sample. The method can include disposing Cyt c on a substrate, contacting the sample with the Cyt c, contacting bound components of the sample with an antibody or antibody fragment specific for LRG, and quantitating the amount of the antibody or antibody fragment bound to LRG.

Referring now to FIG. 1A, a schematic view of an assay in accordance with an embodiment of the invention is shown. Cyt c is disposed on substrate 14. Cyt c can be covalently or non-covalently attached to substrate 14. Substrate 14 can include various components such as a gel, a resin, a bead, nitrocellulose, a nylon membrane, a microtiter plate, a culture flask, a type of polymeric material, or the like. LRG from a sample can then bind to Cyt c forming a complex. By way of example, a sample solution containing LRG may be placed onto the substrate and LRG in the sample solution can then bind to the Cyt c on the substrate. The sample solution can include serum, whole blood, other bodily fluids, samples derived from bodily fluids, or cellular extracts. In some embodiments, unbound components of the sample solution can then be washed away. An antibody 12 can then be added in order to specifically bind LRG. Antibodies in accordance with embodiments of the invention are described in more detail below. The antibody can have a marker 10 directly or indirectly attached to it. Exemplary markers are described in more detail below. Unbound antibody can then be washed away and the marker can be used to identify remaining antibodies 12 that have specifically bound LRG. Antibody 12 can be referred to as a primary antibody. In some embodiments, a secondary antibody is used to detect the primary antibody. For example, referring now to FIG. 1B, a schematic view of an assay is shown with a secondary antibody 22 bound to the primary antibody 12. The secondary antibody 22 can specifically bind the primary antibody 12. The secondary antibody 22 can include a marker 20 for purposes of detection.

Figure 1C:
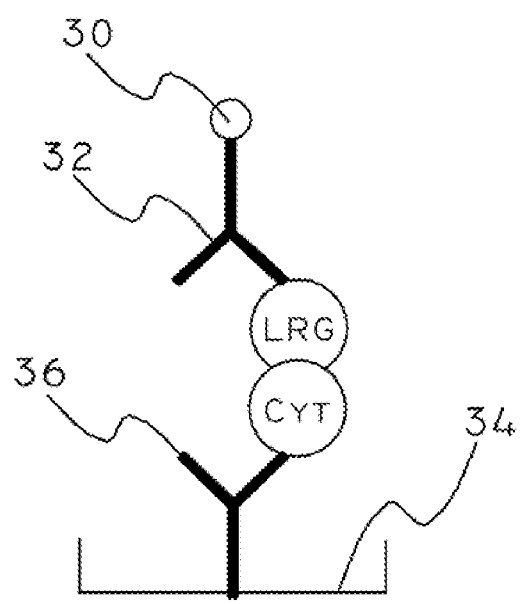

Cyt c may be directly or indirectly bound to the substrate. For example, FIG. 1C, shows a schematic view of an assay in accordance with another embodiment of the invention. In this embodiment, Cyt c is indirectly bound to a substrate 34. Specifically, in this embodiment, an antibody 36 that specifically binds Cyt c is used to bind Cyt c to the substrate 34. LRG is bound to Cyt c in a complex. An antibody 32 specific for LRG, that includes a marker 30, is then bound to LRG.

Figure 1D:
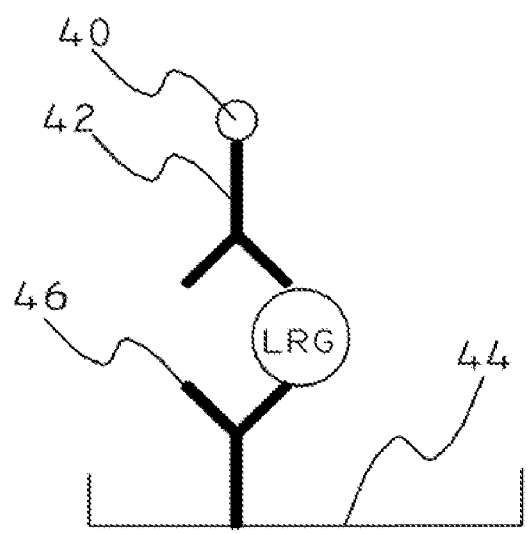

Referring now to FIG. 1D, a schematic view of an assay in accordance with another embodiment of the invention is shown. In this embodiment, the assay is configured to capture LRG that is not bound to Cyt c and, in conjunction with the assay depicted in FIG. 1A, FIG. 1B, or FIG. 1C, can be used to quantify total LRG (both LRG bound to Cyt c in a sample as well as LRG unbound to Cyt c in the sample). In FIG. 1D, an antibody 46 that is specific for LRG is disposed on a substrate 44. LRG in a sample can then bind to antibody 46. LRG that binds to antibody 46 can be detected using another antibody 42 that is specific for LRG. Antibody 42 can include a marker 40.

Figure 1E:
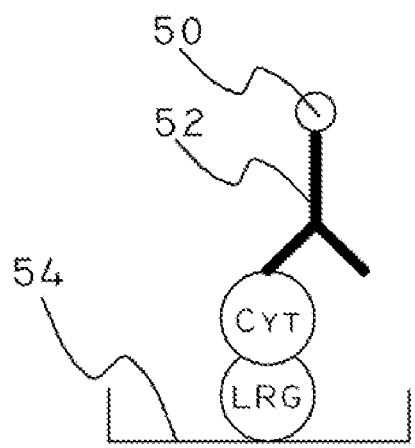

It will be appreciated that assays in accordance with various embodiments of the invention can also be used to identify Cyt c in samples. For example, referring now to FIG. 1E, LRG can be disposed on a substrate 54. Cyt c from a sample can then be bound to LRG forming a complex. By way of example, a sample solution may be poured onto or otherwise contacted with the substrate and Cyt c in the sample solution can bind to the LRG disposed on the substrate. An antibody 52 specific for Cyt c can then bind to Cyt c. The antibody can have a marker 50 attached to it for purpose of detection. Alternately, a secondary antibody with a marker can be used for purposes of detection.

Figure 1F:
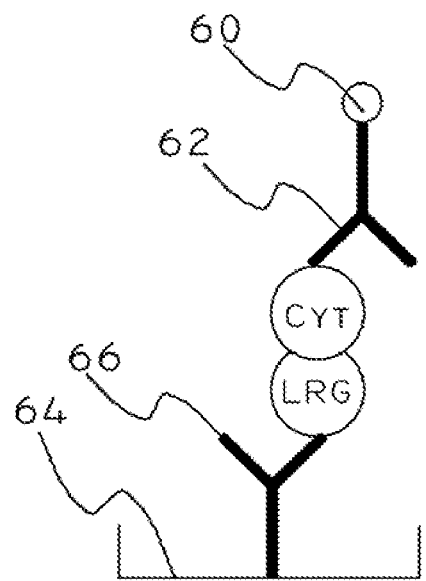

It will be appreciated that LRG used to detect Cyt c can be either directly or indirectly attached to the substrate. Referring now to FIG. 1F, a schematic view of an assay in accordance with another embodiment of the invention is shown. In this embodiment, LRG is indirectly bound to a substrate 64. Specifically, in this case, an antibody 66 that specifically binds LRG is used to bind LRG to the substrate 34. Cyt c from a sample is then bound to LRG forming a complex. An antibody 62 specific for Cyt c, such as one that includes a marker 60, is then bound to Cyt C.

Figure 1G:
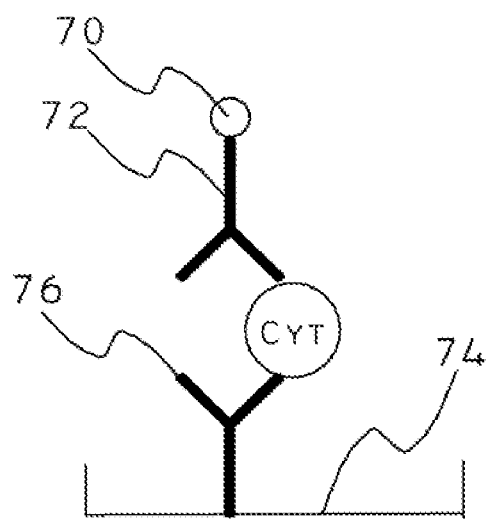

Referring now to FIG. 1G, a schematic view of an assay in accordance with another embodiment of the invention is shown. In this embodiment, the assay is configured in order to capture free Cyt c (not bound to LRG) and, in conjunction with the assay depicted in FIG. 1E or FIG. 1F or FIG. 1C, can be used to quantify total Cyt c. In FIG. 1G an antibody 76 that is specific for Cyt c is disposed on a substrate 74. Cyt c from a sample can then bind to antibody 76. Cyt c that binds to antibody 76 can be detected using another antibody 72 that is specific for Cyt c. Antibody 72 can include a marker 70.

Figure 1H:
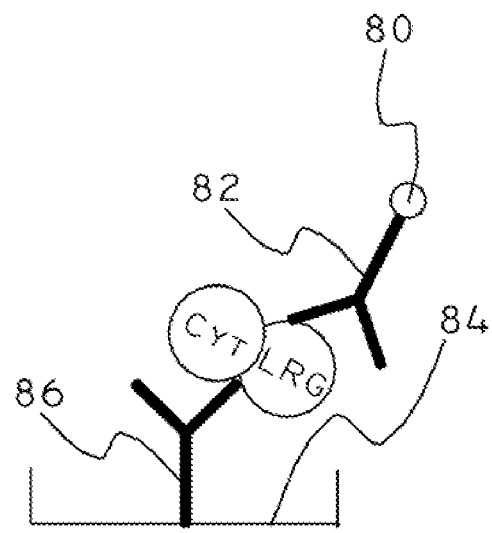

Antibodies that bind specifically to a complex of Cyt c and LRG, as opposed to Cyt c or LRG individually, can also be used in various embodiments of assays. For example, referring now to FIG. 1H, a schematic view of an assay is shown where an antibody 86 specific for the complex of Cyt c and LRG is used to bind Cyt c/LRG complexes from a sample. The complex of Cyt c and LRG can then be identified by an antibody 82 specific for LRG. The antibody 82 can include a marker 80. Alternatively, the complex of Cyt c and LRG can also be identified by an antibody specific for Cyt c, or an antibody specific for the complex of Cyt c and LRG.

LRG, as used in embodiments of the invention and as detected by embodiments of the invention can include human LRG, murine LRG, rat LRG, equine LRG, bovine LRG, and the like. It has been shown that human and bovine LRG bind Cyt c (Cummings et al., Apoptosis, 2006; 11: 1121-1129, published on-line May 9, 2006). The complete primary structure of LRG present in human plasma is known (see Takahashi et al., Proc Natl Acad Sci USA. 1985 Apr;82(7):1906-10). This protein, in its secreted form, consists of a single polypeptide chain with one galactosamine and four glucosamine oligosaccharides attached. The polypeptide has two intrachain disulfide bonds and contains 312 amino acid residues of which 66 are leucine. The amino acid sequence can be exactly divided into 13 segments of 24 residues each, eight of which exhibit a periodic pattern in the occurrence of leucine, proline, and asparagine. The consensus sequence for the repeating tetracosapeptide unit is Pro-Xaa-Xaa-Leu-Leu-Xaa-Xaa-Xaa -Xaa-Xaa-Leu-Xaa-Xaa-Leu-Xaa-Leu-Xaa-Xaa-Asn-Xaa-Leu-Xaa-Xaa-Leu (SEQ ID NO: 1) see Kobe and Kajava, Curr. Op. Struct. Biol., 2001; 11: 725-732). The cDNA sequence for both murine and human leucine-rich 2-glycoprotein (LRG) are known (see O'Donnell et al., Journal of Leukocyte Biology. 2002;72:478-485). The amino acid sequence for human LRG is shown below in Table I (eight leucine-rich repeat motifs are indicated by underlining). The leader sequence (boxed) is cleaved from the polypeptide prior to post-translational glycosylation and secretion of the protein. The secreted protein contains 312 amino acid residues.

TABLE I (SEQ ID NO: 2)

```
  1 msswsrqrpk spggiqphvs rtlfllllla asawdvtlsp kdcqvfrsdh gssiscqppa
 61 eipgylpadt vhlaveffnl thlpanllqg asklgelhls sngleslspe flrpvpqlrv
121 ldltrnaltg lppglfqasa tldtlvlken qlevlevswl hglkalghld lsgnrlrklp
181 pgllanftll rtldlgengl etlppdllrg plglerlhle gnklgvlgkd lllpqpdlry
241 lflngnklar vaagafqglr gldmldlsnn slasvpeglw aslgqpnwdm rdgfdisgnp
301 wicdqnlsdl yrwlqaqkdk mfsqndtrca gpeavkgqtl lavalsq
```

The deduced amino acid sequence of bovine LRG based on the genomic sequence is shown in Table II. In comparison with human LRG, bovine LRG contains an additional 38 amino acids at the amino terminus. However, except for those additional 38 amino acid residues, human and bovine LRG share 71% amino acid sequence identity. Cleavage of the underlined residues at the NEC1 /NEC2 cleavage site (carboxyl terminal to residue 81) results in the mature polypeptide that was purified by adsorption of BSA or fetal bovine serum on Cyt c (Cummings et al., Apoptosis, 2006; 11: 1121-1129. The eight leucine-rich repeat motifs are indicated by underlining.

TABLE II (SEQ ID NO: 3)

```
  1 mallrspqkl aeeqqlqqdl hlaleraeye htktkflspk slsqspinnl pqddadiisf
 61 vtftagirpp cgtkgtwmkk reatmssqnp erkqslvgwd shlsriflll lfvvsaqglt
121 pnpeaclvfs svngssiscq ppaqiphslp adtiflavef fnltqlpadf lqgvpnlqel
181 hlssnrledf spkfllpvpq lkvldltrns ltglfpgffr vsaalctlvl kgnqlkflea
241 swlhglkalr hldlsenqlh slppgllenf tdlltldlsn nglqtlppdl lrgplnlerl
301 hlegnrlqvl gegllapqpk lrylflndnr lasvaagafr glqkldmldl snnllttvpt
361 glwtslgkaa rnlkdgfdis nnpwicdqnl adlyrwlvan enkmffrnht rcagpealkg
421 qtllaaaesh
```

Cyt c, as used in embodiments of the invention and as detected by embodiments of the invention can include many different orthologs including human Cyt c, murine Cyt c, rat Cyt c, bovine Cyt c, equine Cyt c, and the like. The amino acid sequence of human Cyt c including a leading methionine residue is shown in Table III below. The amino acid sequence of the mature form (without the leading methionine residue) of human Cyt c contains 104 amino acid residues with an acetylated amino terminal glycine (shown in position 2 of the sequence below) and heme prosthetic group bound to the polypeptide through cysteines at positions 14 and 17 (positions 15 and 18 in the sequence below) in the mature protein.

TABLE III (SEQ ID NO: 4)

```
  1 mgdvekgkki fimkcsqcht vekggkhktg pnlhglfgrk
    tgqapgysyt aanknkgiiw 61 gedtlmeyle npkkyipgtk mifvgikkke eradliaylk
    katne
```

Antibodies

Aspects of the present invention can include antibodies, including antibodies or antibody fragments that specifically bind Cyt c and antibodies or antibody fragments that specifically bind LRG. An intact antibody molecule has two heavy (H) chain variable regions (abbreviated herein as $V_H$) and two light (L) chain variable regions (abbreviated herein as $V_L$). The $V_H$ and $V_L$ regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al., J. Mol. Biol. 1987;196: 901-917). Each $V_H$ and $V_L$ is composed of three CDR's and four FRs, arranged from amino-terminus to carboxy-terminus in the following order: FR1, CDR1, FR2, CDR2, FR3, CDR3, FR4.

Antibodies of the present invention include various antibody fragments, also referred to as antigen binding fragments, which include only a portion of an intact antibody, generally including an antigen binding site of the intact antibody and thus retaining the ability to bind antigen. Examples of antibody fragments include, for example, Fab, Fab', Fd, Fd', Fv, dAB, and F(ab')$_2$ fragments produced by proteolytic digestion and/or reducing disulfide bridges and fragments produced from an Fab expression library. Such antibody fragments can be generated by techniques well known in the art. Antibodies of the present invention can include the variable region(s) alone or in combination with the entirety or a portion of the hinge region, CH1 domain, CH2 domain, CH3 domain and/or Fc domain(s).

Antibodies of the present invention include, but are not limited to, polyclonal antibodies, affinity-purified polyclonal antibodies, monoclonal antibodies, human antibodies, humanized antibodies, chimeric antibodies, anti-idiotypic antibodies, multispecific antibodies, single chain antibodies, single-chain Fvs (scFv), disulfide-linked Fvs (dsFv), Fab fragments, F(ab') fragments, F(ab')$_2$ fragments, Fv fragments, diabodies, linear antibodies fragments produced by a Fab expression library, fragments comprising either a VL or VH domain, intracellularly-made antibodies (i.e., intrabodies), and antigen-binding antibody fragments thereof.

The antibodies of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In some embodiments, the immunoglobulin is an IgG1 isotype. In other embodiments, the immunoglobulin is an IgG2 isotype. In yet other embodiments, the immunoglobulin is an IgG4 isotype. Immunoglobulins can have both heavy and light chains. An array of IgG, IgE, IgM, IgD, IgA, and IgY heavy chains can be paired with a light chain of the kappa or lambda form.

The antibodies of the invention can be from any animal origin, including birds and mammals. In some embodiments, the antibodies are human, murine, rat, donkey, sheep, rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins.

The term "polyclonal antibody" refers to an antibody produced from more than a single clone of plasma cells. In contrast "monoclonal antibody" refers to an antibody produced from a single clone of plasma cells. The preparation of polyclonal antibodies is well known. Polyclonal antibodies may be obtained by immunizing a variety of warm-blooded animals such as horses, cows, goats, sheep, dogs, chickens, rabbits, mice, hamsters, guinea pigs and rats as well as transgenic animals such as transgenic sheep, cows, goats or pigs, with an immunogen. The resulting antibodies may be isolated from other proteins by using an affinity column having an Fc binding moiety, such as protein A, or the like.

Monoclonal antibodies can be obtained by various techniques familiar to those skilled in the art. For example, spleen cells from an animal immunized with a desired antigen are immortalized, commonly by fusion with a myeloma cell (see, for example, Kohler and Milstein, *Eur. J.Immunol.* (1976);6: 511-519; J. Goding (1986) In "Monoclonal Antibodies: Principles and Practice," Academic Press, pp 59-103; and Harlow et al., Antibodies: A Laboratory Manual, page 726 (Cold Spring Harbor Pub. 1988). Monoclonal antibodies can be isolated and purified from hybridoma cultures by techniques well known in the art. Other known methods of producing transformed B cell lines that produce monoclonal antibodies may also be used.

As used herein, "isolated" refers to material removed from its original environment (e.g., the natural environment if it is naturally occurring), and thus is altered "by the hand of man" from its natural state.

In some embodiments, the antibody can be recombinantly produced, for example, produced by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809. Such methods can be used to generate human monoclonal antibodies.

Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein. See, for example, WO 91/00906; WO 91/10741; WO 92/03918, Lonberg et al., *Nature* (1994);368: 856-859; Green et al., *Nature Genet* (1994);7: 13-21; Morrison et al., *PNAS* (1994);81: 6851-6855; Tuaillon et al., *PNAS* (1993);90:3720-3724; Bruggeman et al., *Eur J Immunol* (1991);21:1323-1326.

A therapeutically useful antibody may be derived from a "humanized" monoclonal antibody. Humanized monoclonal antibodies are produced by transferring one or more CDRs from the heavy and light variable chains of a mouse (or other species) immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found, for example, in Jones et al., *Nature* (1986);321: 522 and Singer et al., *J. Immunol.*, (1993);150: 2844. The constant region of a humanized monoclonal antibody of the present invention can be that from human immunoglobulin belonging to any isotype. It may be, for example, the constant region of human IgG. The framework regions of the constant region derived from human immunoglobulin are not particularly limited.

Antibodies of the present invention include chimeric antibodies. A chimeric antibody is one in which different portions are derived from different animal species. For example, chimeric antibodies can be obtained by splicing the genes from a mouse antibody molecule with appropriate antigen specificity together with genes from a human antibody molecule of appropriate biological specificity. See, for example, Takeda et al., *Nature* (1985);314: 544-546.

The present invention includes bispecific or bifunctional antibodies. A bispecific or bifunctional antibody is an artificial hybrid antibody having two different heavy/light chain pairs and two different binding sites. Bispecific antibodies can be produced by a variety of methods including fusion of hybridomas or linking of F(ab') fragments. See, e.g., Songsivilai & Lachmann, Clin. Exp. Immunol. 79:315-321 (1990), Kostelny et al., J. Immunol. 148:1547 1553 (1992). In addition, bispecific antibodies can be formed as "diabodies" (Holliger et al., PNAS USA 90:6444-6448 (1993)) or "Janusins" (Traunecker et al., EMBO J. 10:3655-3659 (1991) and Traunecker et al., Int. J. Cancer Suppl. 7:51-52 (1992)).

Antibodies of the present invention can be produced, for example, by an animal, chemically synthesized, or recombinantly expressed. Antibodies of the present invention can be purified by any method known in the art for purification of an immunoglobulin molecule, for example, by chromatography (e.g., ion exchange, affinity, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Antibodies of the present invention can be assayed for immunospecific binding by the methods described herein and by any suitable method known in the art. The immunoassays that can be used include but are not limited to competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see e.g., Ausubel et al, eds, Current Protocols in Molecular Biology, Vol. 1, John Wiley & Sons, Inc., N.Y. (1994)).

"Binding affinity" or "affinity binding" refers to the strength of the sum total of noncovalent interactions between a single binding site of a molecule (e.g., an antibody) and its binding partner (e.g., an antigen or antigenic epitope). The affinity of a molecule X for its partner Y is represented by the dissociation constant (Kd), which can generally be determined by using methods known in the art, for example, using the BIAcore biosensor, commercially available from BIAcore Inc., Piscataway, N.J. Antibodies of the present invention include antibodies with binding affinities with a dissociation constant or $K_D$ less than or equal to $5 \times 10^{-2}$ M, less than or equal to $10^{-2}$ M, less than or equal to $5 \times 10^{-3}$ M, less than or equal to $10^{-3}$ M, less than or equal to $5 \times 0^{-4}$ M, less than or equal to $10^{-4}$ M, less than or equal to $5 \times 10^{-5}$ M, less than or equal to $10^{-5}$ M, less than or equal to $5 \times 10^{-6}$ M, less than or equal to $10^{-6}$ M, less than or equal to $5 \times 10^{-7}$ M, less than or equal to $10^{-7}$ M, less than or equal to $5 \times 10^{-8}$ M, less than or equal to $10^{-8}$ M, less than or equal to $5 \times 10^{-9}$ M, less than or equal to $10^{-9}$ M, less than or equal to $5 \times 10^{-10}$ M, less than or equal to $10^{-10}$ M, less than or equal to $5 \times 10^{-11}$ M, less than or equal to $10^{-11}$ M, less than or equal to $5 \times 10^{-12}$ M, less than or equal to $10^{-12}$ M, less than or equal to $5 \times 10^{-13}$ M, less than or equal to $10^{-13}$ M, less than or equal to $5 \times 10^{-14}$ M, less than or equal to $10^{-14}$ M, less than or equal to $5 \times 10^{-15}$ M, or less than or equal to $10^{-15}$ M.

In some embodiments, antibodies of the present invention may have a binding affinity with a dissociation constant or $K_D$ less than or equal to $5 \times 10^{-6}$ M, less than or equal to $10^{-6}$ M, less than or equal to $5 \times 10^{-7}$ M, less than or equal to $10^{-7}$ M, less than or equal to $5 \times 10^{-8}$ M, less than or equal to $10^{-8}$ M, less than or equal to $5 \times 10^{-9}$ M, less than or equal to $10^{-9}$ M, less than or equal to $5 \times 10^{-10}$ M, or less than or equal to $10^{-10}$ M. In some embodiments, antibodies of the present invention may have a binding affinity with a dissociation constant or $K_D$ in the range of about $10^{-6}$ M to about $10^{-10}$ M or of about $10^{-6}$ M to about $10^{-9}$ M.

Antibodies of the present invention include derivatives of antibodies that are modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivatives can contain one or more non-classical amino acids.

Antibodies of the present invention can be recombinantly fused to a heterologous polypeptide at the N- or C-terminus or chemically conjugated, including covalent and non-covalent conjugations, to polypeptides or other compositions. For example, antibodies of the present invention can be recombinantly fused or conjugated to molecules useful as markers in detection assays, or as effector molecules such as heterologous polypeptides, drugs, radionuclides, or toxins. See, for example, WO 92/08495; WO 91/14438; WO 89/12624; U.S. Pat. No. 5,314,995; and EP 0 396 387.

Antibodies of the present invention may be coupled directly or indirectly to a detectable marker by techniques well known in the art. For example, the antibody may be coupled indirectly through an intermediate such as, for example, a linker known in the art, using techniques known in the art. See, for example, U.S. Pat. No. 4,741,900, describing the conjugation of metal ions to antibodies for diagnostic use. A detectable marker is an agent detectable by spectroscopic, photochemical, biochemical, immunochemical, or chemical means. A detectable marker often generates a measurable signal, such as radioactivity, fluorescent light, color, or enzyme activity. Exemplary detectable markers can include fluorescent dyes, chemi- or bio-luminescent compounds, radioisotopes, electron-dense reagents, enzymes, colored particles, biotin, dioxigenin, various prosthetic groups, positron emitting metals using various positron emission tomographies, and nonradioactive paramagnetic metal ions.

Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferase, luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such therapeutic moieties to antibodies are well-known.

Also included in the present invention are hybridoma cell lines, transformed B cell lines and host cells that produce the antibodies of the present invention, the progeny or derivatives of these hybridomas, and equivalent or similar hybridomas.

The present invention further provides an isolated polynucleotide molecule having a nucleotide sequence encoding an antibody of the invention. The present invention is further directed to an isolated polynucleotide molecule comprising a nucleotide sequence that has at least 75%, at least 80%, at least 85%, at least 90%, at least 95%, at least 96%, at least 97%, at least 98%, or at least 99% sequence identity to nucleotide sequence encoding an antibody of the invention. The invention also encompasses polynucleotides that hybridize under high stringency to a nucleotide sequence encoding an antibody of the invention, or a complement thereof. As used herein "stringent conditions" refer to the ability of a first polynucleotide molecule to hybridize, and remain bound to, a second, filter-bound polynucleotide molecule in 0.5M NaHPO$_4$, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). Also included in the present invention are polynucleotides that encode one or more of the CDR regions or the heavy and/or light chains of an antibody of the present invention. General techniques for cloning and sequencing immunoglobulin variable domains and constant regions are well known. See, for example, Orlandi et al., Proc. Nat'l Acad. Sci. USA 86: 3833 (1989).

The present invention also includes recombinant vectors including an isolated polynucleotide of the present invention. The vector can be, for example, in the form of a plasmid, a viral particle, or a phage. The appropriate DNA sequence can be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art, and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector can be used.

The present invention also includes host cells containing the above-described vectors. The host cell can be a higher eukaryotic cell, such as a mammalian or insect cell, or a lower eukaryotic cell, such as a yeast cell. Or, the host cell can be a prokaryotic cell, such as a bacterial cell. Introduction of a vector construct into the host cell can be effected by any suitable techniques, such as, for example, calcium phosphate transfection, DEAE-Dextran mediated transfection, or electroporation. (Davis, L., et al., Basic Methods in Molecular Biology, (1986)).

Antibodies of the present invention can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

Antibodies of the present invention can specifically bind to Cyt c. For example, antibodies of the present invention can specifically bind to human Cyt c, murine Cyt c, rat Cyt c, equine Cyt c, bovine Cyt c, amongst others. Many antibodies that specifically bind Cyt c are commercially available. By way of example antibodies that can specifically bind Cyt c include 2B5 available from R & D Systems Inc., Minneapolis, Minn., and 6H2 available from BD Pharmingen, San Diego, Calif., respectively.

Antibodies of the present invention can specifically bind to LRG. For example, antibodies of the present invention can specifically bind to human LRG, murine LRG, rat LRG, equine LRG, bovine LRG, amongst others. As a specific example, antibodies that specifically bind to human LRG include those produced by the hybridoma having ATCC accession number PTA-8131.

The invention also provides a kit including the antibodies of the present invention. The kit can include one or more containers filled with one or more of the antibodies of the invention. Additionally, the kit may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well known methods, preferably to provide a sterile, contaminant-free environment. As used herein, the term "package" refers to a solid matrix or material such as glass, plastic, paper, foil, and the like, capable of holding within fixed limits a polypeptide. Thus, for example, a package can be a glass vial used to contain milligram quantities of an antibody.

Embodiments of the invention can also include methods of purifying components from a sample, or methods of increasing the purity of such components. By way of example, embodiments of the invention can include methods of purifying LRG from a sample. The method can specifically include contacting the sample with Cyt c. The Cyt c can be disposed a substrate, such as on a bead or a polymer. The method can include forming a complex between LRG in the sample and Cyt c. For example, a sample containing LRG can be combined with the Cyt c and incubated for a period of time. The method can also include removing uncomplexed components of the sample. For example, the uncomplexed components can be washed away. The method can include releasing LRG from the complex with Cyt c and collecting the released LRG. It will be appreciated that embodiments of methods for purifying as described herein can also include various other procedures typically associated with affinity chromatography.

Unless otherwise specified, "a," "an," "the," and "at least one" are used interchangeably and mean one or more than one.

The present invention is illustrated by the following examples. It is to be understood that the particular examples, materials, amounts, and procedures are to be interpreted broadly in accordance with the scope and spirit of the invention as set forth herein.

EXAMPLES

Example 1

Serum Leucine-Rich Alpha-2-Glycoprotein-1 Binds Cytochrome c and Inhibits Antibody Detection of this Apoptotic Marker in Enzyme-Linked Immunosorbent Assay Materials and Methods Human Cyt c was obtained from R & D Systems, Inc. Rat and horse Cyts c, bovine serum albumin (BSA), horseradish peroxidase (HRP)-conjugated goat anti-mouse IgG, Lipidex 1000 (hydroxyalkoxypropyl-dextran Type VI), and all other reagents were obtained from Sigma-Aldrich, unless stated otherwise. Horse and fetal bovine sera were obtained from Gibco-Invitrogen and Biotechnics Research, Inc., respectively. Human and mouse sera were obtained from living donors. mAbs employed in this study were prepared as previously described (Goshorn et al., J. Biol. Chem. 1991; 266: 2134-2142) and purified by affinity chromatography using Cyt c coupled to CNBr-activated Sepharose 4B (Urbanski and margoliash, J. Immunology 1977; 118: 1170-1180).

The sandwich ELISA utilized mAbs directed against two different epitopes on Cyt c. In this assay a mAb against one Cyt c epitope was attached to a well of an assay plate, followed by either the Cyt c antigen itself or serum/BSA mixed with Cyt c. A mAb against the second epitope tagged with HRP was used to detect Cyt c bound in the well employing the catalytic activity of HRP. In the sandwich ELISA for human Cyt c, mAb 2B5, specific for the region around residues 44/47, was used to capture Cyt c and mAb 2G8, specific for the region around residues 60/62, was used to detect bound Cyt c. For detection of mouse/rat Cyt c mAbs 1G1 and 2G8 were employed in the sandwich ELISA. The mAbs used to capture Cyt c were adsorbed to Nunc Immunosorb 96-well plates (Gibbco Scientific, Coon Rapids, Minn.) at 2.5 micrograms/milliliter ($\mu$g/ml) in 50 microliter ($\mu$l) phosphate-buffered saline (PBS).

Antigen capture (approximately 8 nanomolar (nM)) occurred in a total volume of 75 $\mu$l containing 1 mg/ml BSA (greater than 99% pure). The mAbs used for detection were covalently coupled to HRP as has been described (Engvall, Meth. Enzymol. 1980; 70: 419-439) and were used at 150-600 fold dilutions in 1 mg/ml BSA (>99% pure). All incubations were for at least 1-2 hours (hrs) and plates were washed twice in PBS containing 0.1% Triton X-100 between each incubation. The HRP reaction was carried out for 15 minutes with 100 $\mu$l hydrogen peroxide (30% stock solution, 0.5$\mu$l/ml) in citrate-phosphate buffer pH 5.0 and o-phenylenediamine (0.4 mg/ml), followed by 50 $\mu$l 4 normal (N) sulfuric acid to stop the reaction (Engvall, Meth. Enzymol. 1980; 70: 419-439). The absorbance at 492 nm was recorded.

The serum inhibitory factor was first precipitated from fetal bovine serum in saturated ammonium sulfate (60-80% cut). The precipitate was resolubilized and dialysed against 10 mM phosphate pH 7.0. The dialysate was bound to diethylaminoethyl (DEAE) Sephacel and eluted at 65 mM sodium chloride in a step gradient to 200 mM. The major peak was dialyzed against 10 mM ammonium bicarbonate, lyophilized, and applied to a Sephadex G-100 column (50×1.5 cm) equilibrated in PBS, pH 7.4. The factor was partially purified from human serum following a similar protocol: 50-80% saturated ammonium sulfate cut and elution from DEAE-Sephacel between 50 and 70 mM sodium chloride in 10 mM sodium phosphate, pH 7.0. The final step involved affinity chromatography on horse Cyt c-Affi-Gel 10 (see below).

The amino terminal amino acid sequence of the major protein in the inhibitory fraction of fetal bovine serum was determined by Edman degradation employing a Hewlett Packard 241 Protein Sequencer.

Since the inhibitory factor in fetal bovine serum co-purified with BSA in preliminary experiments, a commercial preparation of impure BSA (96-99% pure) was used to isolate the factor by adsorbing it to horse Cyt c coupled to Affi-Gel 10 (Bio-Rad Laboratories). Lysozyme coupled to Affi-Gel 10 was employed as a control. The adsorbents were each coupled to 2 ml of gel at a density of 5 mg/ml. The BSA preparations (greater than 99% pure and 96-99% pure, less than 40 mg/ml in PBS) were incubated on the columns for 1 hour followed by washing of the columns with 20 ml PBS. Bound material was eluted in 0.5 M acetic acid, frozen at −80° C., and lyophilized. To remove lipids, BSA (40Mg, 96-99% pure) in 50 mM potassium phosphate, pH 7.4 was passed through a column containing 1.4 ml Lipidex 1000 at 37° C. (Glatz and Veerkamp, J. Biochem. Biophys. Methods 1983; 8: 57-61).

SDS-PAGE was performed using 4-20% Precise Pre-cast gels and protein bands were stained using GelCode Blue (Pierce Biotechnology). Precision Plus Protein Standards were obtained from Bio-Rad.

Gel slices containing the inhibitory factor cut from a polyacrylamide gel were in-gel digested overnight in 5% trypsin (Promega, Madison, Wisc.). The eluate from Cyt c-Affi-Gel 10. was similarly digested. The digests were desalted using C18 ZipTips (Millipore, Billerica, Mass.). Matrix assisted laser desorption ionization time-of-flight mass spectrometry (MALDI-TOF MS) and MS/MS were then performed (Cotter, Time-of-Flight Mass Spectrometry: Instrumentation and Applications in Biological Research, American Chemical Society, 1996). Full scans of the peptide mixtures from 500-3500 m/z and tandem mass spectral data of selected ions were collected on a QSTAR quadruple TOF mass spectrometer with an orthogonal MALDI source (Applied Biosystems, Inc., Foster City, Calif.) using alpha-cyano-4-hydroxycinnamic acid as the matrix. Mass spectra were averaged from approximately 50-100 laser shots collected in positive mode.

Results

Sera from different species (horse, human, mouse, and fetal bovine sera) were examined for inhibition of rat and human Cyt c detection in the sandwich ELISA. Inhibition of Cyt c detection in ELISA was observed with sera from all species tested as shown in FIG. 2 in the detection of rat Cyt c. Slight inhibition was observed at serum concentrations below 1% and was essentially complete at 10%. Similar results were observed in the sandwich ELISA employed to detect human Cyt c.

Since gamma globulin-free horse serum was also inhibitory in this assay, the factor responsible is not a naturally-occurring antibody reactive with Cyt c (see FIG. 2). It was conceivable that inhibition could have been caused by Cyt c present in the sera. However, the mAbs used for capture of rat Cyt c in the sandwich ELISA do not cross-react with the Cyts c of all the species tested. Furthermore, if that were the case, mouse serum would have increased the absorbance values in ELISA rather than decreasing them since mouse and rat Cyts c are identical (Carlson et al., Biochemistry 1977; 16: 1437-1442).

The results shown in FIG. 2 were obtained employing a Cyt c concentration of 8 nM. In other experiments not shown inhibition was observed employing a range of Cyt c concentrations from 1 nM to 500 nM. The concentration of Cyt c in normal human serum has been reported to be 1.9 ng/ml or 0.15 nM (Pullerits et al., Rheumatology 2005; 44: 32-39) and may be elevated several hundred-fold in sera of patients with apoptosis-associated diseases (Renz et al., Blood 2001; 98: 1542-1548; Barczyk et al., Int. J. Cancer 2005; 116: 167-173; Gvatua et al., Ter. Arkh. 1990; 62: 58-61; Alleyne et al., Appl. Biochem. Biotech. 2001; 90: 97-105; Ben-Ari et al., J. Intern. Med. 2003; 254: 168-175; Adachi et al., Clin. Chim. Acta 2004; 342: 127-136; and Nunoi et al., Pediatr. Int. 2005; 47: 175-179). The real values may actually be higher than the measured values due to the effect of the serum inhibitory factor in the ELISA.

Figure 3:
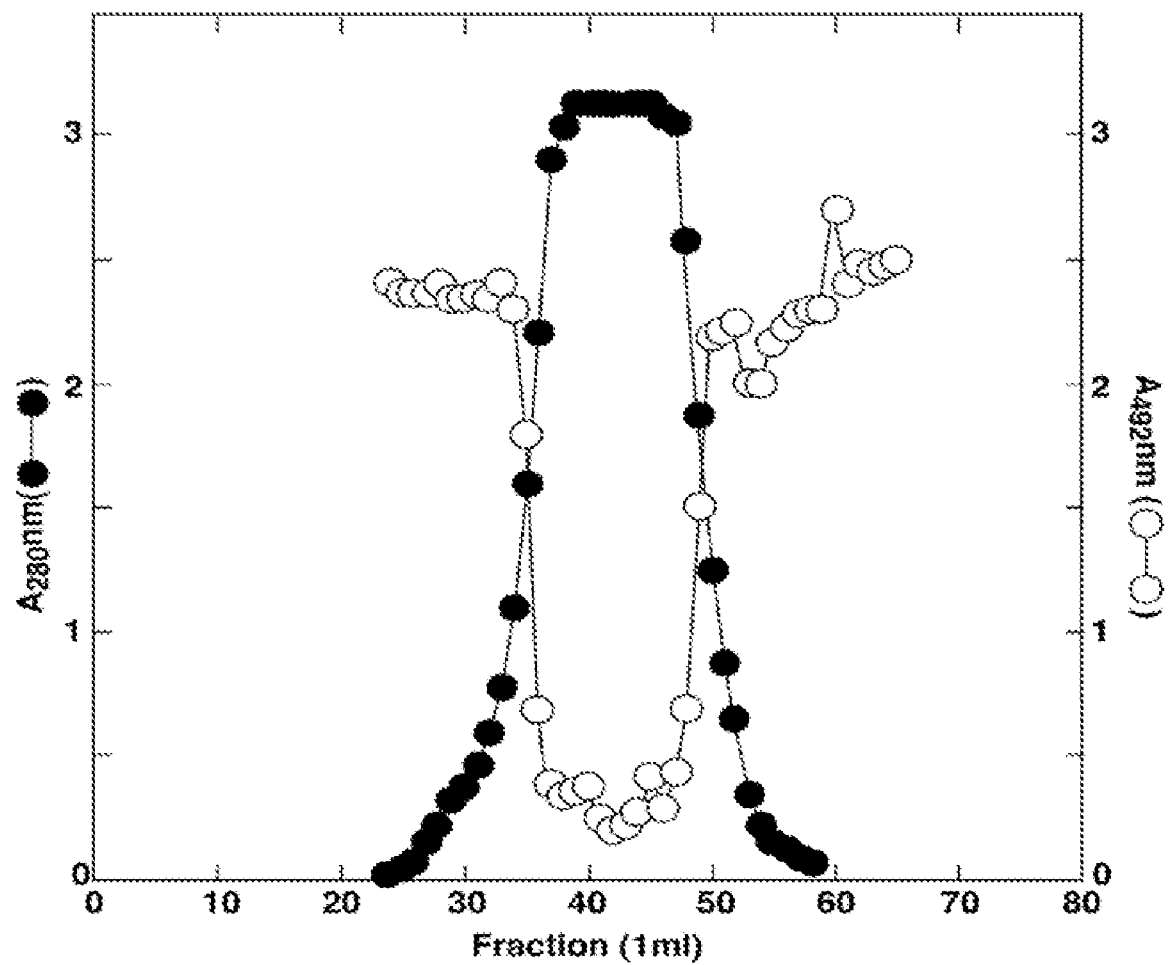
FIG. 3 demonstrates the partial purification using conventional biochemical methods of the factor in fetal bovine serum that inhibits the detection of rat Cyt c in sandwich ELISA, later identified as LRG. Total protein ($A_{280\ nm}$) and effect on rat Cyt c detection in sandwich ELISA ($A_{492\ nm}$) are plotted for each fraction. The protein-containing fractions (●, closed circles) from the last purification step, gel filtration chromatography on Sephadex G-100, correspond to the inhibitory fractions (○, open circles).

Initial attempts to purify the inhibitory component by direct adsorption of horse serum or fetal bovine serum on Cyt c-coupled Affi-Gel 10 resulted in multiple polypeptides eluting from the column as observed in SDS-PAGE. Furthermore, there was no specificity in the adsorption pattern in that the same bands were observed in the eluate from lysozyme-coupled Affi-Gel 10. Lysozyme is an appropriate control since it is approximately the same size as Cyt c and has a similar pI. Therefore, work proceeded to purify the inhibitory component from fetal bovine serum using a variety of methods and testing the fractions at each purification step for inhibition in sandwich ELISA. This approach included protein precipitation in saturated ammonium sulfate, ion exchange chromatography using DEAE, and gel filtration chromatography using Sephadex G-100 (see Materials and Methods). Inhibition of Cyt c detection in sandwich ELISA (FIG. 3, open circles) corresponded to the major fraction eluting from the gel filtration column, the last purification step (FIG. 3, closed circles).

The fraction corresponding to the highest A280 from the Sephadex G-100 column (fraction 40 from a parallel run) was subjected to N-terminal amino acid sequencing. The sequence of the first 10 residues was determined to be DTH-KSEIAHR (SEQ ID NO: 5), the amino terminal sequence of the mature bovine serum albumin (BSA) polypeptide chain as searched employing BLAST (basic local alignment search tool) (Brown, Fed. Proc. 1975; 34: 591-591).

Figure 4:
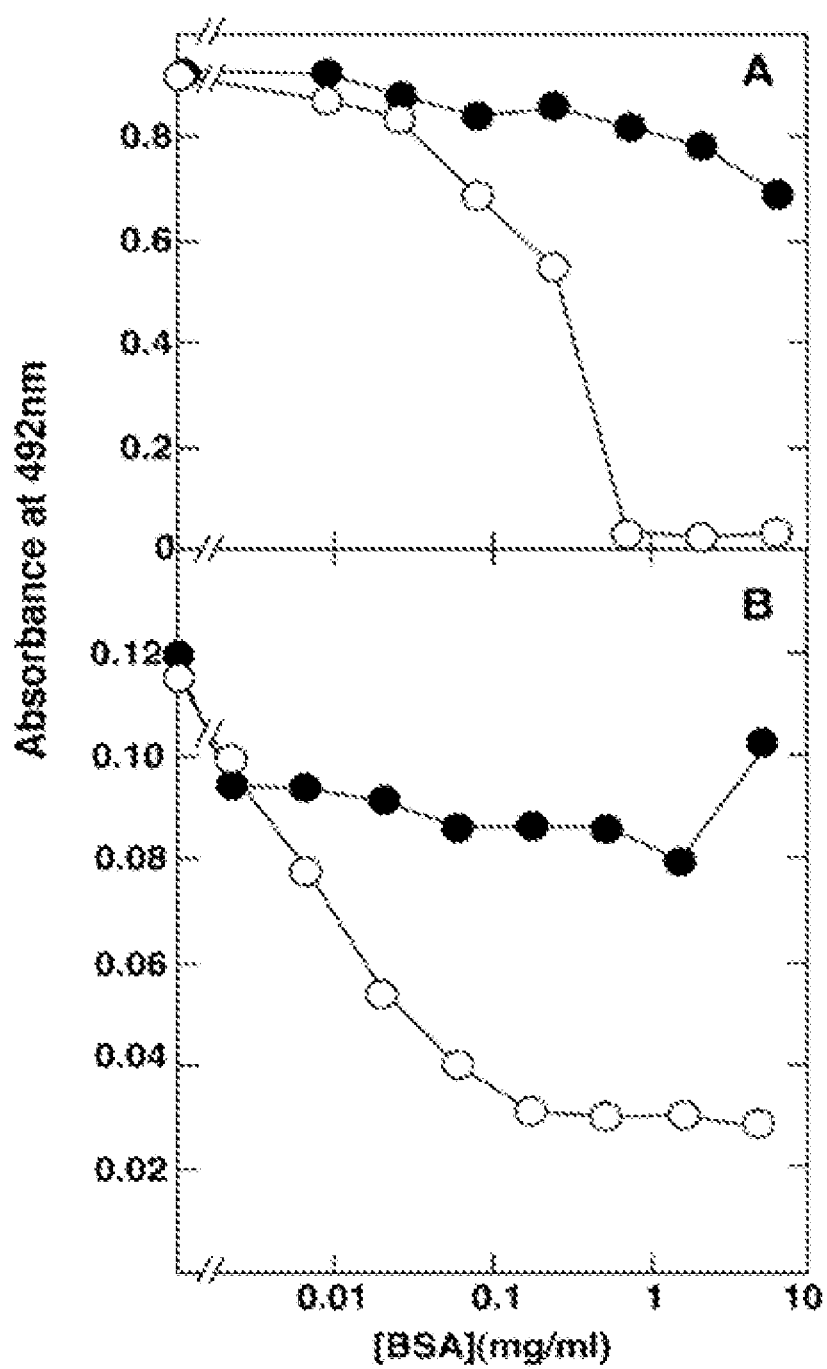
FIGS. 4A and 4B demonstrate that BSA, 96-99% pure (○), inhibits the detection of rat Cyt c in sandwich ELISA much more effectively than the fatty acid-free form (>99%, ●) suggesting that either a fatty acid bound to BSA or some other contaminant in the commercial BSA preparation interferes with Cyt c detection, later identified as LRG. The difference between BSA and the fatty acid-free form was observed whether (FIG. 4A) mAb 1G1 was used for capture and mAb 2G8-HRP was used for detection or (FIG. 4B) mAb 2G8 was used for capture and mAb 1G1-HRP was used for detection. The values plotted represent the averages of triplicate readings with an average S.D.=0.058.

BSA obtained from a commercial source (96-99% pure) was also found to have an inhibitory effect on Cyt c detection in the sandwich ELISA (FIG. 4, open circles). As was the case for serum, the inhibition by this preparation of BSA was observed whether mAb 1G1 or mAb 2G8 was used to capture rat Cyt c. The lowest concentration of the 96-99% pure BSA that resulted in complete inhibition of Cyt c detection in ELISA represents a molar ratio of approximately 1:1000 (Cyt c:BSA) suggesting that the inhibitory factor is a minor component in this BSA preparation.

A more pure form of BSA (>99%, essentially fatty acid free) obtained from the same supplier was tested and found that it was much less inhibitory than the 96-99% pure BSA (FIG. 4, closed circles). This indicates that the inhibitory effect is due either to a minor component associated with BSA in the less pure preparation, such as a lipid, or to a contaminant that co-purifies with BSA.

No inhibition by serum or BSA (96-99% pure) was observed if either were incubated with the capture antibody and then removed from the assay plate before the addition of Cyt c. This indicates that the inhibitory component did not bind the antibody and block the capture of Cytc.

Since BSA is a well-known lipid carrier, Lipidex 1000 was used to adsorb lipids from BSA (96-99% pure) (Glatz and Veerkamp, J. Biochem. Biophys. Methods 1983; 8: 57-61). As shown in Table IV, this treatment failed to remove the inhibitory component indicating that it is probably not a lipid. The effect of the effluent on rat Cyt c detection in sandwich ELISA was essentially the same as the effluent from Sephadex G-25. The extensive dialysis used in the purification of the inhibitory fraction containing BSA (FIG. 3) would argue against some other small molecule inhibitor that was not bound to a larger molecular weight component in this material.

TABLE IV

Inhibition by BSA (96-99% pure) of rat Cyt c detection in sandwich ELISA was eliminated by pre-adsorption on horse Cyt c-Affi-Gel 10, but not on Lipidex.

| Inhibitor | A492 nm |
| --- | --- |
| No BSA | 0.625 ± 0.088 |
| BSA[a] (96-99% pure) adsorbed on: | |
| Lysozyme coupled Affi-Gel | 0.026 ± 0.003 |
| Cyt c coupled Affi-Gel | 0.622 ± 0.005 |
| Lipidex | 0.104 ± 0.019 |
| Sephadex | 0.093 ± 0.026 |

[a]BSA (96-99% pure) was tested at a concentration of 0.5 mg/ml.

To determine if the inhibitory component bound Cyt c, horse Cyt c coupled to Affi-Gel was tested for its ability to remove the inhibitory component from BSA (96-99% pure). As shown in Table V, following passage through a 1.5 ml column of Cyt c coupled Affi-Gel, there was very little inhibition remaining in the BSA preparation. In contrast, incubation with lysozyme failed to remove the inhibitory component. From this experiment, one can conclude that the inhibitory component binds Cyt c. Furthermore, the acid eluate, following lyophilization and neutralization, was found to contain the inhibitory component (Table V).

TABLE V

Inhibitory activity adsorbed on Cyt c-Affi-Gel 10 is retained following acid elution.

| Eluant of: | $A_{492\ nm}$ in sandwich ELISA for rat Cyt c |
| --- | --- |
| BSA (96-99% pure) adsorbed on Cyt c[a] | 0.075 ± 0.004 |
| BSA (96-99% pure) adsorbed on lysozyme | 0.250 ± 0.004 |
| BSA (>99% pure) adsorbed on Cyt c | 0.225 ± 0.040 |
| BSA(>99% pure) adsorbed on lysozyme | 0.235 ± 0.004 |

[a]Eluates were diluted 1:3 for the data reported. Further dilutions yielded less inhibition.

Identification of the Inhibitory Factor in Bovine Serum

Figure 5:
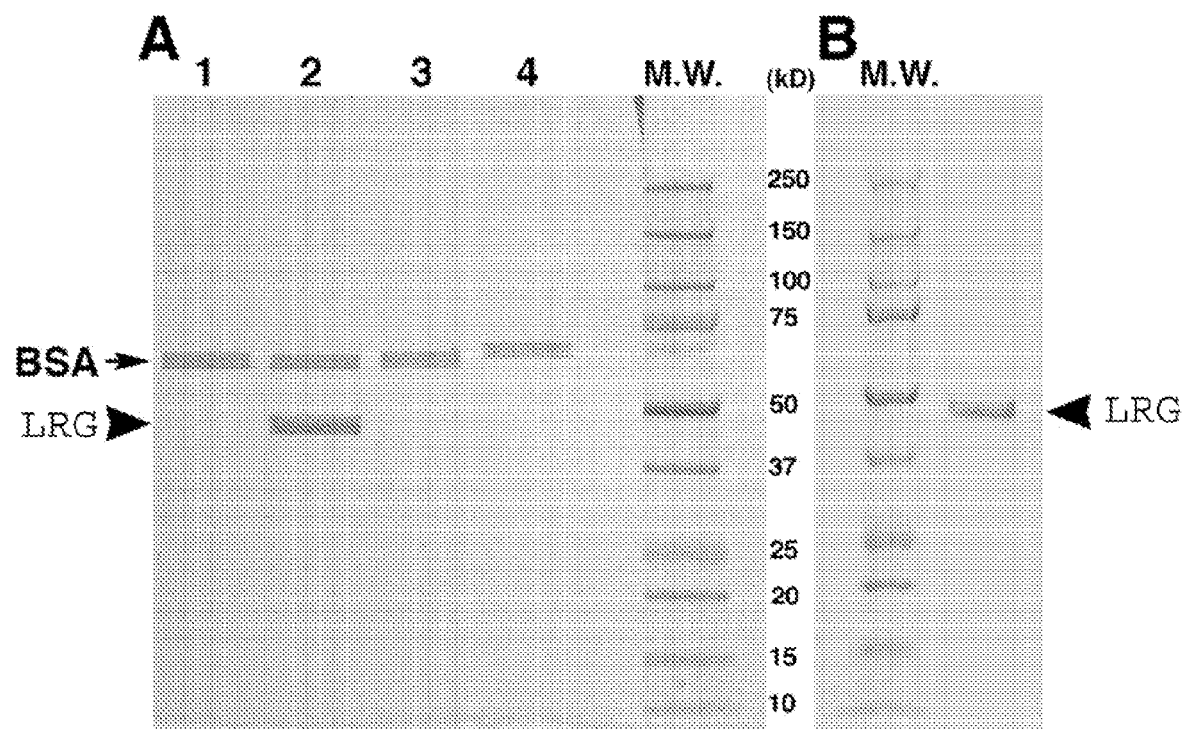
FIGS. 5A and 5B are SDS-PAGE (polyacrylamide gel electrophoresis in sodium dodecylsulfate) of polypeptides either once adsorbed from BSA onto Cyt c-Affi-Gel 10 or lysozyme-Affi-Gel 10 and eluted in 0.5 M acetic acid (FIG. 5A) or twice adsorbed onto Cyt c-Affi-Gel 10 and eluted (FIG. 5B) showing that the serum inhibitory factor, later identified as LRG, can be removed from a solution by adsorption on Cyt c.

Proteins adsorbed from 96-99% pure BSA by the Cyt c-coupled Affi-Gel were eluted in 0.5 M acetic acid, lyophilized, and examined in SDS-PAGE. Although comparable small amounts of BSA from both the 99% pure and 96-99% pure preparations did adsorb to both the Cyt c and lysozyme coupled Affi-Gel columns, possibly due to electrostatic interactions between the negatively charged BSA and positively charged adsorbants (FIG. 5, arrow), there was a protein band at approximately 44 kD that was specifically adsorbed to the Cyt c coupled Affi-Gel column (FIG. 5A, lane 2, arrowhead). This component was not adsorbed from >99% pure BSA by either lysozyme (FIG. 5A, lane 3) or Cyt c (FIG. 5A, lane 4) and was not adsorbed by lysozyme from 96-99% pure BSA (FIG. 5A, lane 1). A second adsorption on Cyt c of the eluate from 96-99% pure BSA initially adsorbed on and eluted from Cyt c allowed for further enrichment of the 44 kD protein relative to BSA (FIG. 5B, arrowhead). This isolate had similar inhibitory activity as the initial eluate (A492 nm=0.059±0.008 at the same dilution tested, see Table V).

Mass spectrometry analysis of tryptic peptides of the 44 kD polypeptide excised from the polyacrylamide gel (FIG. 5, lane 2) identified it as bovine leucine-rich alpha-2-glycoprotein-1 (LRG; NCBI BLAST gi/61878169) (Table VI). The tryptic peptides observed in MALDI-TOF MS encompass 42% of the length of the polypeptide chain predicted from the genomic sequence. The MASCOT score (www.matrixscience.com) of 193 is statistically significant (for scores >68, p<0.05). MS/MS analysis of nine peptides yielded a cumulative ions score of 238. MALDI-TOF analysis of tryptic peptides from the total eluate from the Cyt c-Affi-Gel column also yielded a statistically significant score of 105 (for scores >47, p<0.05) with 42% polypeptide coverage.

No peptide sequences upstream of residue 82 in the predicted amino acid sequence were observed (Table VI). It would appear that the mature polypeptide that was isolated derives from enzymatic cleavage of a precursor at the NEC1/NEC2 (proprotein convertases 1 and 2) cleavage site, carboxyl terminal to the sequence "KR" at residues 80-81. Although cDNA analysis of human and mouse LRG predicted the amino terminus at position 85, not at position 82 as observed in the present experiments, that methodology may not have allowed for isolation of full-length cDNA encompassing the amino terminal segment (O'Donnell et al., J. Leuk. Biol. 2002; 72: 478-485). The sequence isolated from bovine serum albumin initiates 37 amino acid residues upstream from human LRG that was isolated from human serum two decades ago (Takahashi et al., Proc. Natl. Acad. Sci. USA 1985; 82: 1906-1910). The higher molecular weight of the observed polypeptide versus the predicted polypeptide (residues 82-430) is approximately 9 kD consistent with glycosylation. There are 8 leucine-rich repeats in bovine LRG with the consensus sequence "LXLXXNXL" (SEQ ID NO: 6) that is shared by other leucine-rich proteins (Kobe and Kajava, Curr. Op. Struct. Biol. 2001; 11: 725-732).

TABLE VI

MALDI-TOF analysis of the bovine inhibitory factor identifies it as LRG.

| Residue Numbers | Observed M.W.[a] | Predicted M.W. | Amino Acid Sequence |
| --- | --- | --- | --- |
| 82-93[b] | 1376.68 | 1376.64 | EATMSSQNPERK (Residues 82-93 of SEQ ID NO: 3) |
| 194-202 | 1053.68 | 1053.66 | FLLPVPQLK (Residues 194-202 of SEQ ID NO: 3) |
| 203-208 | 715.42 | 715.42 | VLDLTR (Residues 203-208 of SEQ ID NO: 3) |

TABLE VI-continued

MALDI-TOF analysis of the bovine inhibitory factor identifies it as LRG.

| Residue Numbers | Observed M.W.[a] | Predicted M.W. | Amino Acid Sequence |
|---|---|---|---|
| 209-220 | 1354.7 | 1354.7 | NSLTGLFPGFFR (Residues 209-220 of SEQ ID NO: 3) |
| 221-231 | 1173.66 | 1173.68 | VSAALCTLVLK (Residues 221-231 of SEQ ID NO: 3) |
| 237-247 | 1299.7 | 1299.7 | FLEASWLHGLK (Residues 237-247 of SEQ ID NO: 3) |
| 293-299 | 797.44 | 797.44 | GPLNLER (Residues 293-299 of SEQ ID NO: 3) |
| 300-306 | 837.45 | 837.45 | LHLEGNR (Residues 300-306 of SEQ ID NO: 3) |
| 300-320 | 2281.27 | 2281.29 | LHLEGNRLQVLGEGLLAPQPK (Residues 300-320 of SEQ ID NO: 3) |
| 307-320 | 1461.86 | 1461.86 | LQVLGEGLLAPQPK (Residues 307-320 of SEQ ID NO: 3) |
| 321-330 | 1322.68 | 1322.71 | LRYLFLNDNR (Residues 321-330 of SEQ ID NO: 3) |
| 323-330 | 1053.54 | 1053.52 | YLFLNDNR (Residues 323-330 of SEQ ID NO: 3) |
| 331-340 | 961.54 | 961.53 | LASVAAGAFR (Residues 331-340 of SEQ ID NO: 3) |
| 345-368 | 2617.35 | 2617.37 | LDMLDLSNNLLTTVPTGLWTSLGK (Residues 345-368 of SEQ ID NO: 3) |
| 372-395 | 2880.35 | 2880.35 | NLKDGFDISNNPWICDQNLADLYR (Residues 372-395 of SEQ ID NO: 3) |
| 375-395 | 2525.12 | 2525.13 | DGFDISNNPWICDQNLADLYR (Residues 375-395 of SEQ ID NO: 3) |
| 396-403 | 972.5 | 972.5 | WLVANENK (Residues 396-403 of SEQ ID NO: 3) |
| 412-430 | 1922.95 | 1922.95 | CAGPEALKGQTLLAAAESH (Residues 412-430 of SEQ ID NO: 3) |
| 420-430 | 1096.55 | 1096.55 | GQTLLAAAESH (Residues 420-430 of SEQ ID NO: 3) |

[a]M.W., molecular weight

Identification of the inhibitory factor in human serum.

The inhibitory factor was also isolated from human serum using a purification scheme similar to that followed for bovine LRG, including adsorption on Cyt c-Affi-Gel 10. Unlike 96-99% BSA, the inhibitory factor was not observed in 96-99% human serum albumin that was obtained from the same commercial source. In sandwich ELISA the acid eluate (lyophilized and neutralized) inhibited detection of rat Cyt c ($A_{492\ nm}$=0.352±0.07 in the absence of the eluate and $A_{492\ nm}$=0.079±0.015 in the presence of a 1 to 10 dilution of the lyophilized eluate in PBS, further dilution yielded less inhibition.

Figure 6:
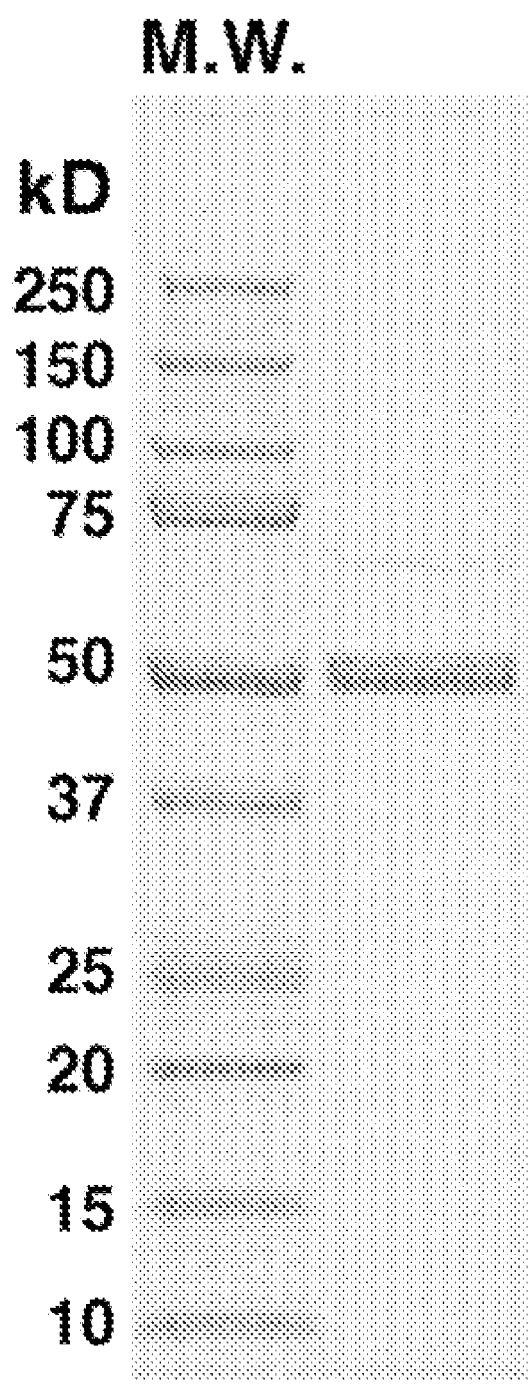
FIG. 6 is an SDS-PAGE of the human serum inhibitory factor following acid elution from Cyt c-Affi-Gel 10. The minor band near 70 kD was identified by matrix-assisted laser desorption ionization time-of-flight (MALDI-TOF) mass spectrometry as hemopexin which apparently bound some Cyt c molecules, possibly denatured during previous acid elution. In subsequent experiments minor contaminants such as this were removed using hydroxylapatite as previously described (Haupt and Baudner, Hoppe-Seyler's Z. Physiol. Chem. 1977; 358: 639-646). The amount of eluate applied to the gel is approximately equal to that contained in 0.7 ml serum.

Two bands were observed in SDS-PAGE (FIG. 6). The major band at 50 kD was identified by MALDI-TOF MS as human LRG (Table VII; NCBI BLAST gi/72059) and the minor band near 70 kD was identified as hemopexin. The MASCOT score for LRG was 142 (for scores >69, p<0.05) with 57% sequence coverage. MS/MS analysis of two peptides (ALGHLDLSGNR (SEQ ID NO: 7) and LHLEG-NKLQVLGK (SEQ ID NO: 8) yielded significant individual ions scores of 52 and 67, respectively (for scores >47, p<0.05). Hemopexin may have been present as a minor contaminant in the preparation due to adsorption to some denatured Cyt c molecules on the Affi-Gel column. In native Cyt c the heme is buried except for an edge (Sanishvili et al., Structure 1995; 3: 707-716) and is not accessible for binding hemopexin. Denaturation of some Cyt c molecules on the adsorption column may have occurred during prior acid elutions. Adsorption of a separate preparation of the inhibitory factor on a freshly prepared Cyt c-Affi-Gel column that was not previously acid washed enriched for the 50 kD band, while some Cyt c molecules not covalently bound to the Affi-Gel also eluted during the acid wash.

TABLE VII

MALDI-TOF analysis of the human inhibitory factor identifies it as LRG.

| Residue Numbers | Observed M.W.[a] | Predicted M.W. | Amino Acid Sequence |
|---|---|---|---|
| 42-47[b] | 823.36 | 823.3647 | DCQVFR (Residues 42-47 of SEQ ID NO: 2) |
| 94-119 | 2958.6336 | 2958.5926 | LQELHLSSNGLESLSPEFLRPVPQLR (Residues 94-119 of SEQ ID NO: 2) |
| 120-125 | 715.4191 | 715.4228 | VLDLTR (Residues 120-125 of SEQ ID NO: 2) |
| 149-164 | 1893.0097 | 1892.9995 | ENQLEVLEVSWLHGLK (Residues 149-164 of SEQ ID NO: 2) |
| 165-175 | 1151.6091 | 1151.6047 | ALGHLDLSGNR (Residues 165-175 of SEQ ID NO: 2) |
| 165-177 | 1420.7893 | 1420.7898 | ALGHLDLSGNRLR (Residues 165-177 of SEQ ID NO: 2) |
| 192-209 | 2036.0951 | 2036.0789 | TLDLGENQLETLPPDLLR (Residues 192-209 of SEQ ID NO: 2) |
| 192-216 | 2829.5572 | 2829.5236 | TLDLGENQLETLPPDLLRGPLQER (Residues 192-216 of SEQ ID NO: 2) |
| 210-216 | 811.4542 | 811.4552 | GPLQLER (Residues 210-216 of SEQ ID NO: 2) |

TABLE VII-continued

MALDI-TOF analysis of the human inhibitory factor identifies it as LRG.

| Residue Numbers | Observed M.W.[a] | Predicted M.W. | Amino Acid Sequence |
|---|---|---|---|
| 217-229 | 1447.8298 | 1447.851 | LHLEGNKLQVLGK (Residues 217-229 of SEQ ID NO: 2) |
| 230-239 | 1178.6654 | 1178.6659 | DLLLPQPDLR (Residues 230-239 of SEQ ID NO: 2) |
| 230-247 | 2128.1553 | 2128.168 | DLLLPQPDLRYLFLNGNK (Residues 230-247 of SEQ ID NO: 2) |
| 240-247 | 967.5126 | 967.5127 | YLFLNGNK (Residues 240-247 of SEQ ID NO: 2) |
| 240-250 | 1307.7361 | 1307.7349 | YLFLNGNKLAR (Residues 240-250 of SEQ ID NO: 2) |
| 251-260 | 988.5475 | 988.5453 | VAAGAFQGLR (Residues 251-260 of SEQ ID NO: 2) |
| 292-312 | 2484.1133 | 2484.1015 | DGFDISGNPWICDQNLSDLYR (Residues 292-312 of SEQ ID NO: 2) |
| 313-318 | 772.4123 | 772.4232 | WLQAQK (Residues 313-318 of SEQ ID NO: 2) |
| 329-345 | 1711.9338 | 1711.929 | CAGPEAVKGQTLLAVAK (Residues 329-345 of SEQ ID NO: 2) |

[a]M.W., molecular weight
[b]Residue 42 is equivalent to residue 7 in the reported protein sequence (Takahashi et al., Proc. Natl. Acad. Sci. USA 1985; 82: 1906-1910).

This example shows that a component in serum binds Cyt c and inhibits its ability to be recognized by antibodies, thus decreasing the sensitivity of Cyt c detection in antibody-based assays such as sandwich ELISA. This component was present in the sera of all four species that were tested including human, cow, horse, and mouse.

Since during the course of purification of this component from fetal bovine serum, the inhibition of each isolated fraction was followed, it would appear that the factor isolated is the major, if not only, component in serum that interferes with the detection of Cyt c in sandwich ELISA.

Although the inhibitory factor isolated from fetal bovine serum co-purified with BSA, since the inhibitory effect was observed with 96-99% pure BSA but not observed with >99% pure BSA, the inhibitor is not albumin itself. Serum albumin is a well-known lipid binding protein that, in particular, binds fatty acids (Spector, J. Lipid Res. 1975; 16: 165-179) and these are essentially absent in the >99% pure preparation. Cyt c is also known to bind fatty acids as well as other lipids, including phospholipids (Tuominen et al., J. Biol. Chem. 2002; 277: 8822-8826). Binding of these small molecules causes a conformational change in Cyt c that affects antibody recognition (Jemmerson et al., Biochem. 1999; 38: 3599-3609). It was possible that lipids could have been transferred from the less pure BSA to Cyt c. However, passage of the 96-99% pure BSA through a Lipidex 1000 column, which effectively removes lipids from proteins, failed to remove the inhibitory activity.

By adsorption of the 96-99% pure BSA on Cyt c coupled to Affi-Gel 10, the inhibitory component was removed and shown by SDS-PAGE to be a 44 kD protein. From mass spectrometry analyses it was identified as bovine LRG. The human homolog of this factor (50 kD) was not present in the 96-99% commercial preparation of human serum albumin but that it could be purified from serum employing a similar procedure as was used to isolate the bovine protein.

Example 2

Preparation of Antibodies to LRG and Detection of LRG Protein in Human Neutrophils To obtain polyclonal antibodies, mice were immunized intraperitoneally with 50 µg human LRG protein, purified from human plasma, covalently coupled to hemocyanin using glutaraldehyde (Jemmerson, J. Immunol., 1987; 138:213-219), and emulsified in complete Freund's adjuvant. Serum samples were obtained from the mice between 5 and 8 weeks after initial injection where a booster challenge occurred at week 3 and the sera were tested for binding to the HL-60 cell line, a cell line which when incubated for several days in 1.25% dimethylsulfoxide (DMSO) expresses human LRG. See O'Donnell et al. (J. Leuk. Biol. 2002; 72:478-485) for a more detailed discussion. In ELISA the antibodies reacted with human LRG (absorbance at 492 nm=1.06 at a 1:100 dilution and 0.43 at a 1:500 dilution) with weak cross-reactivity to bovine LRG (absorbance at 492 nm=0.27 at a 1:100 dilution and 0.07 at 1:500 dilution with background readings around 0.05).

In indirect immunofluorescence of DMSO-induced HL-60 cells (causing differentiation into granulocytic cells e.g., neutrophils) and of neutrophils isolated from human blood there was punctate labeling, frequently polarized to one side of the cell that appeared at or just beneath the cell surface, consistent with the staining pattern expected of a secreted protein. A subpopulation of neutrophils also showed intense cytoplasmic staining.

Example 3

Preparation of Monoclonal Antibody (2F5.A2) Specific for LRG

Purified human LRG was covalently coupled in an equimolar amount to hemocyanin using glutaraldehyde (Jemmerson, J. Immunol. 1987; 138: 213-219). BALB/c mice were injected i.p. with 25 µg protein emulsified 1:1 in complete Freund's adjuvant and challenged 3 weeks later with the conjugated protein (25 µg) emulsified in incomplete Freund's adjuvant. A monoclonal antibody specific for human LRG (mAb 2F5.A2, determined to express the $\gamma_1$ and κ heavy and light chain isotypes, respectively, by indirect ELISA) was obtained by fusing splenocytes of an immunized mouse three weeks after secondary challenge with P3X63 myeloma cells using polyethylene glycol (Kearney et al., J. Immunol., 1979; 123: 1548-1550). Antibody-secreting hybridomas were selected by ELISA and subcloned in limiting dilution using normal mouse splenocytes as feeder cells. The mAb was purified from ascites fluid in two steps: precipitation in 50% saturated ammonium and flow through DEAE-Sephacel beads in 40 mM sodium phosphate, pH 8.0.

Example 4

Indirect ELISA to Detect LRG Employing Monoclonal Antibody 2F5.A2

Figure 7:
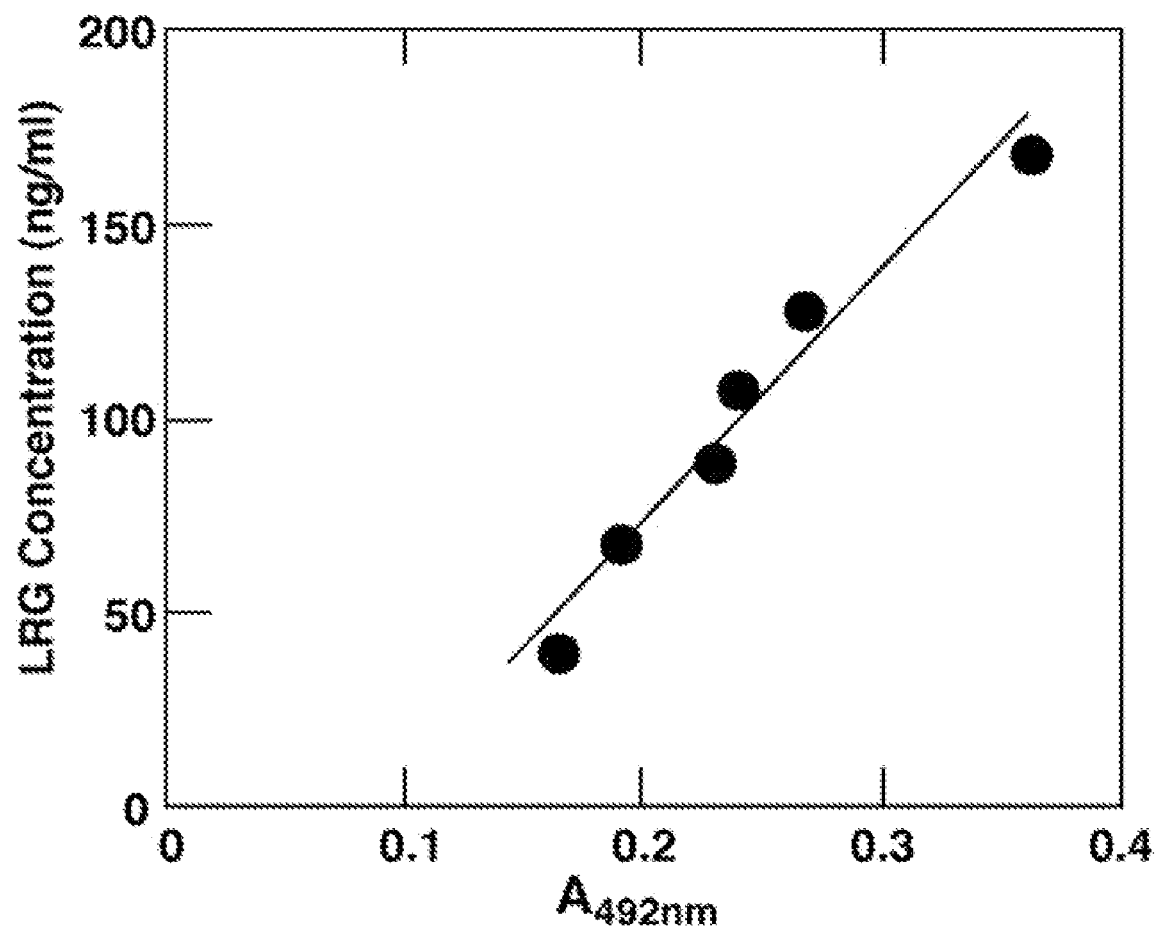
FIG. 7 is a standard curve for LRG quantification in which LRG is detected using the ELISA format shown in FIG. 1B employing monoclonal antibody 2F5.A2 that is produced by a hybridoma cell line deposited with the ATCC (ATCC Accession Number PTA-8131).

Cyt c from a variety of species including horse, cow, rat, rabbit, and human were dissolved at a concentration of 0.5 mM in phosphate-buffered saline, pH 7.4 and 50 ml were adsorbed for 1.5 hrs. to 96 well MaxiSorp plates (Nalge Nunc International, Rochester, N.Y.). The plates were washed twice in phosphate-buffered saline containing 0.1% Triton X-100 then 50 µl 10% human serum or purified LRG standard were added to each well for 1.5 hrs. After two washes, mouse anti-human LRG monoclonal antibody 2F5.A2 (from a hybridoma assigned ATCC Accession Number PTA-8131) was added to each well at a concentration of 0.6 µg/ml and incubated for 1.5 hrs. The plates were washed twice and each well incubated with 50 µl of a 1:2000 dilution of goat anti-mouse IgG (whole molecule) conjugated to horseradish peroxidase (Sigma Chem. Co., St. Louis, Mo.). After 1.5 hrs. the plates were washed three times and citrate-phosphate buffer, pH 5.0 containing substrate (hydrogen peroxide) and color indicator (o-phenylenediamine) was added to each well to 100 µl. The reaction was allowed to continue for 15 min. and stopped by the addition of 50 µl 4 N sulfuric acid. The absorbance at 492 nm was determined employing a Titertek Multiskan plate reader (Flow Laboratories, McClean, Va.). A typical standard curve detecting different concentrations of purified human LRG is shown in FIG. 7.

An assay was then used to quantify LRG in sera of patients with various types of cancer. Specifically, for this assay, horse Cyt c (50 µl, 0.5 µM in PBS) was non-specifically and non-covalently bound to Nunc Maxisorp microtiter plates. After 2 hours, the plates were washed with 0.1% Triton X-100 in PBS. Sera, diluted 1:500, 1:1000, 1:20000, and 1:3000, or purified, human LRG at defined concentrations were then incubated on the plate. After 2 hours of incubation followed by several washes, mAb 2F5.A2 (0.6 µg/ml) was incubated on the plate, followed after several washes by HRP-goat anti-mouse IgG (1:2000 dilution of a commercially-available preparation). Otherwise, the assay was performed in accordance with the procedures described in Example 1. There were 60 control subjects in this study. Values were determined in triplicate with standard deviations less than 10%. The resulting data are shown below in Table VIII.

TABLE VIII

Increased Serum LRG in Some Patients with Cancer

| Patient I.D. | Proliferative Disorder | Serum LRG (µg/ml) |
|---|---|---|
| 3 | cervical polyps | 96 |
| 10 | endometrial adenocarcinoma | 213 |
| 66 | endometrial adenocarcinoma | 50 |
| 19 | breast cancer | 34 |
| 68 | breast cancer | 297 |
| 86 | breast cancer | 100 |
| 80 | fibroma | 26 |
| 88 | fibroma | 167 |
| C1 | ovarian carcinoma | 255 |
| C2 | ovarian carcinoma | 217 |
| C3 | ovarian carcinoma | 162 |
| C6 | ovarian carcinoma | 48 |
| controls | none | 45 |

Example 5

Cyts c from a Variety of Species Bind Human LRG

Horse Cyt c was adsorbed to a microtiter plate and increasing concentrations of Cyt c from various species present in the solution phase were allowed to compete with the plate-bound Cyt c for human LRG binding. Otherwise, the assay was performed in accordance with the procedures described in Example 1.

Figure 8:
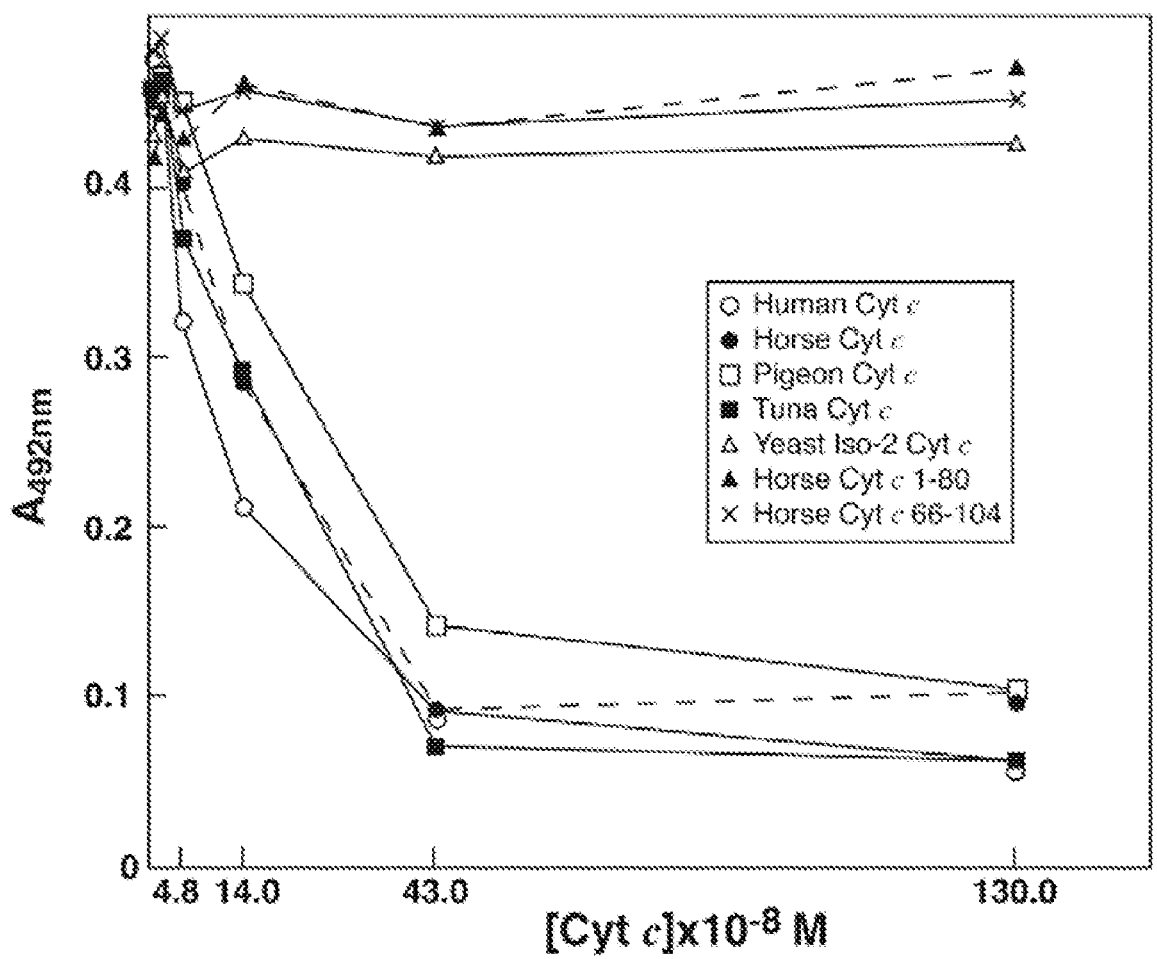
FIG. 8 demonstrates by a competitive ELISA that human LRG binds Cyts c from a variety of species as distant from human as tuna but does not bind yeast Cyt c.

The data is shown in FIG. 8. The data show that human LRG not only binds human Cyt c, but also binds other mammalian Cyts c such as horse Cyt c, a bird (pigeon) Cyt c, and a fish (tuna) Cyt c. These Cyts c are identical in amino acid sequence between residues 63 and 87 with the exception that human Cyt c has valine at position 83 instead of alanine (Borden and Margoliash, in Handbook of Biochemistry and Molecular Biology, 1976; CRC Press, Vol. III, G. D. Fasman, Ed., P. 268). This 25 residue amino acid consensus sequence is shown below in Table IX. As such, in some embodiments of the invention, assays and methods can include a polypeptide including the amino acid sequence of SEQ ID NO: 9.

TABLE IX tlmeylenpk kyipgtkmif xgikk    (SEQ ID NO: 9)

Notably, horse Cyt c shares 88% sequence identity with human Cyt c. Pigeon Cyt c shares 87% sequence identity with human Cyt c. Tuna Cyt c shares 79% sequence identity with human Cyt c. In some embodiments of the invention, assays and methods can include a polypeptide having at least 79% sequence identity with human Cyt c.

Figure 9:
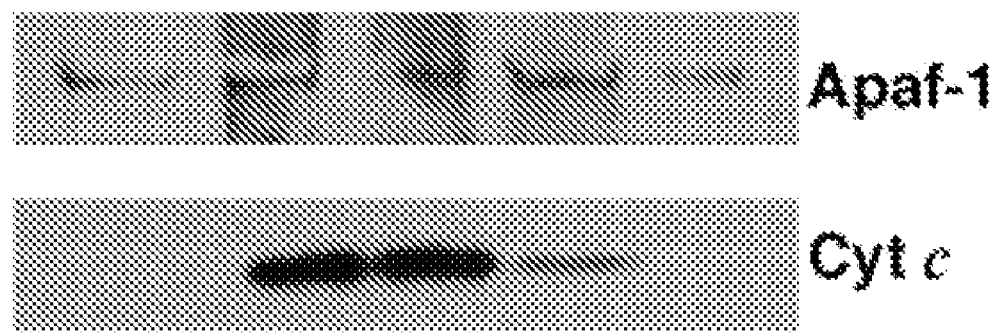
FIG. 9 demonstrates that LRG competes with Apaf-1 for binding Cyt c. Cytosol containing a recombinant form of human Apaf-1 was incubated with increasing amounts of purified human LRG and a constant amount of Cyt c. Apaf-1 and bound ligands were immunoprecipitated using a specific antibody reactive with the Apaf-1 polypeptide and protein G-agarose beads, and the immunoprecipitates were electrophoresed in SDS-PAGE, then transferred electrophoretically to a nitrocellulose membrane for western blotting using antibodies specific for recombinant Apaf-1 (top) or Cyt c (bottom).

Yeast Cyt c which does not bind human LRG has a number of amino acid sequence differences in the region between residues 63 and 87 from the other Cyts c tested. Yeast Cyt c shares 55% sequence identity with human Cyt c. Also, yeast Cyt c is post-translationally modified by tri-methylation at a lysine residue corresponding to residue 72 in human Cyt c. This data alone suggests that LRG binds in the region containing all or part of residues 63 through 87 Residue 72 within this region has been shown to be involved in Apaf-1 binding to Cyt c (Kluck et al., J. Biol. Chem., 2000; 275: 16127-16133). Because Apaf-1 and LRG compete with each other for binding Cyt c (see Example 6; FIG. 9), the region around residue 72 is again implicated in the binding of LRG to Cyt c.

Example 6

LRG Competes with the Pro-Apoptotic Protein Apaf-1 for Binding Cyt

The pro-death activity of Cyt c following its release from mitochondria is dependent on its binding to the cytoplasmic protein, Apaf-1 (Liu et al., Cell, 1996; 86: 147-157). Inhibition of the interaction between Cyt c and Apaf-1 would be a mechanism for survival and has been reported to occur in response to some forms of cell stress by the heat shock protein 27, Hsp 27 (Bruey et al., Nature Cell Biol., 2000; 2: 645-652).

For this example, recombinant human Apaf-1 was obtained from the cytosol of $5 \times 10^7$ murine KL5-12 cells that had been transfected with a construct of the human Apaf-1 gene contiguous to a Myc epitope. The cytosol (70 µl of the 700 µl stock) was incubated with increasing amounts of purified human LRG (0 to 5 µg) and a constant amount of horse Cyt c (0.6 µg). After mixing for 4 hrs. at 4 deg. C., a commercially-available anti-Myc antibody (1 µl) and protein G-agarose beads (20 µl) were added with end-over-end mixing for 2 hrs. The beads were washed three times with 0.5 ml buffer A (Liu et al., Cell, 1996; 86: 147-157.) Proteins bound non-covalently to the beads were released by boiling in detergent (SDS), electrophoresed in SDS-PAGE, and western blotted using anti-Cyt c mAb 7H8.2C12 (Liu et al., Cell, 1996; 86: 147-157) or a commercially-available anti-Apaf-1 antibody followed by HRP-goat anti-mouse IgG. Chemiluminescent detection of HRP enzyme activity was employed to visualize the protein bands. The data in FIG. 9 show that LRG competes with Apaf-1 for binding with Cyt c in vitro. As such, LRG can inhibit the interaction between Cyt c and Apaf-1.

A sequence listing is provided herewith having the filename "Sequence_Listing_ST25.txt", 11 kb in size and created on Jan. 24, 2007, the contents of which is herein incorporated by reference.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. If there is a discrepancy between the specification and a disclosure incorporated by reference, the specification will take precedent. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of detecting leucine-rich alpha-2-glycoprotein-1 (LRG) in a sample, the method comprising:
    disposing Cytochrome c (Cyt c) on a substrate;
    contacting the sample with the Cyt c, wherein the Cyt c disposed on the substrate binds to LRG in the sample;
    contacting bound components of the sample with an antibody or antibody fragment specific for LRG; and
    detecting the antibody or antibody fragment bound to LRG.

2. The method of claim 1, wherein the substrate comprises a gel, a resin, a bead, nitrocellulose, a nylon membrane, a microtiter plate, a culture flask, or a polymeric material.

3. The method of claim 1, wherein the antibody or antibody fragment specific for LRG is detectably labeled.

4. The method of claim 1, wherein the antibody or antibody fragment specific for LRG is labeled with a marker selected from the group consisting of an enzyme, a fluorescent label, radioisotope and biotin.

5. The method of claim 1, wherein detecting the antibody or antibody fragment bound to LRG comprises quantitating the antibody or antibody fragment bound to LRG.

6. The method of claim 1, wherein the Cyt c is directly bound to the substrate.

7. The method of claim 1, wherein the Cyt c is non-covalently bound to the substrate.

8. The method of claim 1, wherein the Cyt c is covalently bound to the substrate.

9. The method of claim 1, wherein the Cyt c is indirectly bound to the substrate.

10. The method of claim 1, wherein the Cyt c is bound to the substrate by a second antibody or antibody fragment specific for Cyt c.

11. The method of claim 1, wherein the sample comprises serum.

12. The method of claim 1, further comprising rinsing away unbound components of the sample after the step of contacting the sample with the Cyt c.

13. The method of claim 1, further comprising rinsing away unbound antibody or antibody fragment after the step of contacting bound components of the sample with an antibody or antibody fragment specific for LRG.

14. The method of claim 1, wherein the antibody or antibody fragment specific for LRG comprises a monoclonal antibody or monoclonal antibody fragment.

15. The method of claim 1, wherein the antibody or antibody fragment specific for LRG is produced by a hybridoma cell line having ATCC Accession Number PTA-8131.

\* \* \* \* \*

```
                              SEQUENCE LISTING

<160> NUMBER OF SEQ ID NOS: 9

<210> SEQ ID NO 1
<211> LENGTH: 24
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid

<400> SEQUENCE: 1

Pro Xaa Xaa Leu Leu Xaa Xaa Xaa Xaa Xaa Leu Xaa Xaa Leu Xaa Leu
1               5                   10                  15

Xaa Xaa Asn Xaa Leu Xaa Xaa Leu
            20

<210> SEQ ID NO 2
<211> LENGTH: 347
<212> TYPE: PRT
<213> ORGANISM: Homo sapiens

<400> SEQUENCE: 2

Met Ser Ser Trp Ser Arg Gln Arg Pro Lys Ser Pro Gly Gly Ile Gln
```

-continued

```
            1               5                  10                 15
        Pro His Val Ser Arg Thr Leu Phe Leu Leu Leu Leu Ala Ala Ser
                     20                  25                 30

Ala Trp Gly Val Thr Leu Ser Pro Lys Asp Cys Gln Val Phe Arg Ser
                     35                  40                 45

Asp His Gly Ser Ser Ile Ser Cys Gln Pro Ala Glu Ile Pro Gly
                     50                  55                 60

Tyr Leu Pro Ala Asp Thr Val His Leu Ala Val Glu Phe Phe Asn Leu
         65                  70                  75                 80

Thr His Leu Pro Ala Asn Leu Leu Gln Gly Ala Ser Lys Leu Gln Glu
                     85                  90                 95

Leu His Leu Ser Ser Asn Gly Leu Glu Ser Leu Ser Pro Glu Phe Leu
                     100                 105                110

Arg Pro Val Pro Gln Leu Arg Val Leu Asp Leu Thr Arg Asn Ala Leu
                     115                 120                125

Thr Gly Leu Pro Pro Gly Leu Phe Gln Ala Ser Ala Thr Leu Asp Thr
                     130                 135                140

Leu Val Leu Lys Glu Asn Gln Leu Glu Val Leu Glu Val Ser Trp Leu
        145                  150                 155                160

His Gly Leu Lys Ala Leu Gly His Leu Asp Leu Ser Gly Asn Arg Leu
                     165                 170                175

Arg Lys Leu Pro Pro Gly Leu Leu Ala Asn Phe Thr Leu Leu Arg Thr
                     180                 185                190

Leu Asp Leu Gly Glu Asn Gln Leu Glu Thr Leu Pro Pro Asp Leu Leu
                     195                 200                205

Arg Gly Pro Leu Gln Leu Glu Arg Leu His Leu Glu Gly Asn Lys Leu
                     210                 215                220

Gln Val Leu Gly Lys Asp Leu Leu Pro Gln Pro Asp Leu Arg Tyr
        225                  230                 235                240

Leu Phe Leu Asn Gly Asn Lys Leu Ala Arg Val Ala Ala Gly Ala Phe
                     245                 250                255

Gln Gly Leu Arg Gln Leu Asp Met Leu Asp Leu Ser Asn Asn Ser Leu
                     260                 265                270

Ala Ser Val Pro Glu Gly Leu Trp Ala Ser Leu Gly Gln Pro Asn Trp
                     275                 280                285

Asp Met Arg Asp Gly Phe Asp Ile Ser Gly Asn Pro Trp Ile Cys Asp
                     290                 295                300

Gln Asn Leu Ser Asp Leu Tyr Arg Trp Leu Gln Ala Gln Lys Asp Lys
        305                  310                 315                320

Met Phe Ser Gln Asn Asp Thr Arg Cys Ala Gly Pro Glu Ala Val Lys
                     325                 330                335

Gly Gln Thr Leu Leu Ala Val Ala Lys Ser Gln
                     340                 345

<210> SEQ ID NO 3
<211> LENGTH: 430
<212> TYPE: PRT
<213> ORGANISM: Bos taurus

<400> SEQUENCE: 3

Met Ala Ala Leu Arg Ser Pro Gly Lys Leu Ala Glu Glu Gln Gly Leu
        1                    5                  10                 15

Gln Gln Asp Leu His Leu Ala Leu Glu Arg Ala Glu Tyr Glu His Thr
                     20                  25                 30
```

Lys Thr Lys Phe Leu Ser Pro Lys Ser Leu Ser Gln Ser Pro Ile Asn
             35                  40                  45

Asn Leu Pro Gln Asp Asp Ala Asp Ile Ile Ser Phe Val Thr Phe Thr
         50                  55                  60

Ala Gly Ile Arg Pro Pro Cys Gln Thr Lys Gly Thr Trp Met Lys Lys
 65                  70                  75                  80

Arg Glu Ala Thr Met Ser Ser Gln Asn Pro Glu Arg Lys Gln Ser Leu
                 85                  90                  95

Val Gly Trp Asp Ser His Leu Ser Arg Ile Phe Leu Leu Leu Leu Phe
             100                 105                 110

Val Val Ser Ala Gln Gly Leu Thr Pro Asn Pro Glu Ala Cys Leu Val
             115                 120                 125

Phe Ser Ser Val Asn Gly Ser Ser Ile Ser Cys Gln Pro Pro Ala Gln
         130                 135                 140

Ile Pro His Ser Leu Pro Ala Asp Thr Ile Phe Leu Ala Val Glu Phe
145                 150                 155                 160

Phe Asn Leu Thr Gln Leu Pro Ala Asp Phe Leu Gln Gly Val Pro Asn
                 165                 170                 175

Leu Gln Glu Leu His Leu Ser Ser Asn Arg Leu Glu Asp Phe Ser Pro
             180                 185                 190

Lys Phe Leu Leu Pro Val Pro Gln Leu Lys Val Leu Asp Leu Thr Arg
         195                 200                 205

Asn Ser Leu Thr Gly Leu Phe Pro Gly Phe Phe Arg Val Ser Ala Ala
         210                 215                 220

Leu Cys Thr Leu Val Leu Lys Gly Asn Gln Leu Lys Phe Leu Glu Ala
225                 230                 235                 240

Ser Trp Leu His Gly Leu Lys Ala Leu Arg His Leu Asp Leu Ser Glu
                 245                 250                 255

Asn Gln Leu His Ser Leu Pro Pro Gly Leu Leu Glu Asn Phe Thr Asp
             260                 265                 270

Leu Leu Thr Leu Asp Leu Ser Asn Asn Gln Leu Gln Thr Leu Pro Pro
         275                 280                 285

Asp Leu Leu Arg Gly Pro Leu Asn Leu Glu Arg Leu His Leu Glu Gly
         290                 295                 300

Asn Arg Leu Gln Val Leu Gly Glu Gly Leu Leu Ala Pro Gln Pro Lys
305                 310                 315                 320

Leu Arg Tyr Leu Phe Leu Asn Asp Asn Arg Leu Ala Ser Val Ala Ala
                 325                 330                 335

Gly Ala Phe Arg Gly Leu Gln Lys Leu Asp Met Leu Asp Leu Ser Asn
             340                 345                 350

Asn Leu Leu Thr Thr Val Pro Thr Gly Leu Trp Thr Ser Leu Gly Lys
         355                 360                 365

Ala Ala Arg Asn Leu Lys Asp Gly Phe Asp Ile Ser Asn Asn Pro Trp
         370                 375                 380

Ile Cys Asp Gln Asn Leu Ala Asp Leu Tyr Arg Trp Leu Val Ala Asn
385                 390                 395                 400

Glu Asn Lys Met Phe Phe Arg Asn His Thr Arg Cys Ala Gly Pro Glu
                 405                 410                 415

Ala Leu Lys Gly Gln Thr Leu Leu Ala Ala Glu Ser His
             420                 425                 430

<210> SEQ ID NO 4
<211> LENGTH: 105
<212> TYPE: PRT

<213> ORGANISM: Homo sapiens

<400> SEQUENCE: 4

Met Gly Asp Val Glu Lys Gly Lys Lys Ile Phe Ile Met Lys Cys Ser
1               5                   10                  15

Gln Cys His Thr Val Glu Lys Gly Gly Lys His Lys Thr Gly Pro Asn
            20                  25                  30

Leu His Gly Leu Phe Gly Arg Lys Thr Gly Gln Ala Pro Gly Tyr Ser
        35                  40                  45

Tyr Thr Ala Ala Asn Lys Asn Lys Gly Ile Ile Trp Gly Glu Asp Thr
    50                  55                  60

Leu Met Glu Tyr Leu Glu Asn Pro Lys Lys Tyr Ile Pro Gly Thr Lys
65                  70                  75                  80

Met Ile Phe Val Gly Ile Lys Lys Lys Glu Glu Arg Ala Asp Leu Ile
                85                  90                  95

Ala Tyr Leu Lys Lys Ala Thr Asn Glu
            100                 105

<210> SEQ ID NO 5
<211> LENGTH: 10
<212> TYPE: PRT
<213> ORGANISM: Bos taurus

<400> SEQUENCE: 5

Asp Thr His Lys Ser Glu Ile Ala His Arg
1               5                   10

<210> SEQ ID NO 6
<211> LENGTH: 8
<212> TYPE: PRT
<213> ORGANISM: Bos taurus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 6

Leu Xaa Leu Xaa Xaa Asn Xaa Leu
1               5

<210> SEQ ID NO 7
<211> LENGTH: 11
<212> TYPE: PRT
<213> ORGANISM: Homo sapiens

<400> SEQUENCE: 7

Ala Leu Gly His Leu Asp Leu Ser Gly Asn Arg
1               5                   10

<210> SEQ ID NO 8
<211> LENGTH: 13
<212> TYPE: PRT
<213> ORGANISM: Homo sapiens

<400> SEQUENCE: 8

Leu His Leu Glu Gly Asn Lys Leu Gln Val Leu Gly Lys

-continued

```
<210> SEQ ID NO 9
<211> LENGTH: 25
<212> TYPE: PRT
<213> ORGANISM: Homo sapiens
<220> FEATURE:
<221> NAME/KEY: misc_feature
<222> LOCATION: (21)..(21)
<223> OTHER INFORMATION: Xaa can be any naturally occurring amino acid

<400> SEQUENCE: 9

Thr Leu Met Glu Tyr Leu Glu Asn Pro Lys Lys Tyr Ile Pro Gly Thr
1               5                   10                  15

Lys Met Ile Phe Xaa Gly Ile Lys Lys
            20                  25
```